United States Patent
Smith et al.

(10) Patent No.: US 10,016,190 B2
(45) Date of Patent: Jul. 10, 2018

(54) MEDICAL DEVICES AND RELATED METHODS OF USE

(71) Applicant: Boston Scientific Scimed, Inc., Maple Grove, MN (US)

(72) Inventors: Paul Smith, Smithfield, RI (US); Mary Ann Cornell, Brimfield, MA (US); Samuel Raybin, Marlborough, MA (US); Robert Devries, Northborough, MA (US); Meghan E. Soens, Lexington, MA (US); Niklas Andersson, Wayland, MA (US); Shawn Ryan, Upton, MA (US); Matthew R. Jagelski, West Roxbury, MA (US); Ray H. Tong, Milford, MA (US); Celine Chin, Brookline, MA (US); Jon Taylor, Groton, MA (US); Daniel E. Hamilton, Mont Vernon, NH (US); Robert Charles, New Boston, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 231 days.

(21) Appl. No.: 14/886,968

(22) Filed: Oct. 19, 2015

(65) Prior Publication Data
US 2016/0038133 A1 Feb. 11, 2016

Related U.S. Application Data

(63) Continuation-in-part of application No. 13/774,719, filed on Feb. 22, 2013, now Pat. No. 9,561,048.
(Continued)

(51) Int. Cl.
*A61B 1/32* (2006.01)
*A61B 17/02* (2006.01)
(Continued)

(52) U.S. Cl.
CPC ...... *A61B 17/0218* (2013.01); *A61B 1/00087* (2013.01); *A61B 1/00089* (2013.01);
(Continued)

(58) Field of Classification Search
CPC .. A61B 1/32; A61B 1/005; A61B 1/10; A61B 1/00135; A61B 1/00137
(Continued)

(56) References Cited

U.S. PATENT DOCUMENTS

| 5,337,754 A | 8/1994 | Heaven et al. |
| 6,139,508 A | 10/2000 | Simpson et al. |
| 2006/0235417 A1 | 10/2006 | Sala |
| 2007/0135686 A1 | 6/2007 | Pruitt, Jr. et al. |

(Continued)

OTHER PUBLICATIONS

International Search Report for corresponding International Application No. PCT/US2013/027439, dated Nov. 6, 2013 (4 pages).

*Primary Examiner* — Ellen C Hammond
*Assistant Examiner* — Christina Negrellirodrigue
(74) *Attorney, Agent, or Firm* — Bookoff McAndrews, PLLC

(57) ABSTRACT

A tissue retractor for attachment to an elongate member of a medical device. The tissue retractor includes a cap having a central longitudinal axis. The cap includes an attachment section adapted to attach to a distal end of the elongate member. The cap further includes a moveable component pivotally attached to the attachment section at one or more pivot points, and an actuator connected to the moveable component to transition the moveable component across the central longitudinal axis from an insertion state to an actuated state.

18 Claims, 14 Drawing Sheets

Related U.S. Application Data

(60) Provisional application No. 61/602,372, filed on Feb. 23, 2012.

(51) Int. Cl.
*A61B 17/32* (2006.01)
*A61B 17/3205* (2006.01)
*A61B 1/00* (2006.01)
*A61B 17/00* (2006.01)

(52) U.S. Cl.
CPC .. *A61B 1/00101* (2013.01); *A61B 17/320016* (2013.01); *A61B 17/32056* (2013.01); *A61B 2017/00269* (2013.01); *A61B 2017/00867* (2013.01); *A61B 2017/320044* (2013.01)

(58) Field of Classification Search
USPC ....... 600/101, 104, 127, 562, 564, 566, 567, 600/210, 214; 606/45, 46, 167, 170
See application file for complete search history.

(56) References Cited

U.S. PATENT DOCUMENTS

| | | |
|---|---|---|
| 2008/0058590 A1 | 3/2008 | Saadat et al. |
| 2008/0269557 A1 | 10/2008 | Marescaux et al. |
| 2009/0076498 A1* | 3/2009 | Saadat ............... A61B 18/1492 606/41 |
| 2010/0168610 A1* | 7/2010 | Lacombe ............... A61B 1/018 600/564 |
| 2010/0274275 A1 | 10/2010 | Stammberger et al. |
| 2011/0060188 A1 | 3/2011 | Sharon et al. |
| 2011/0098531 A1 | 4/2011 | To |

* cited by examiner

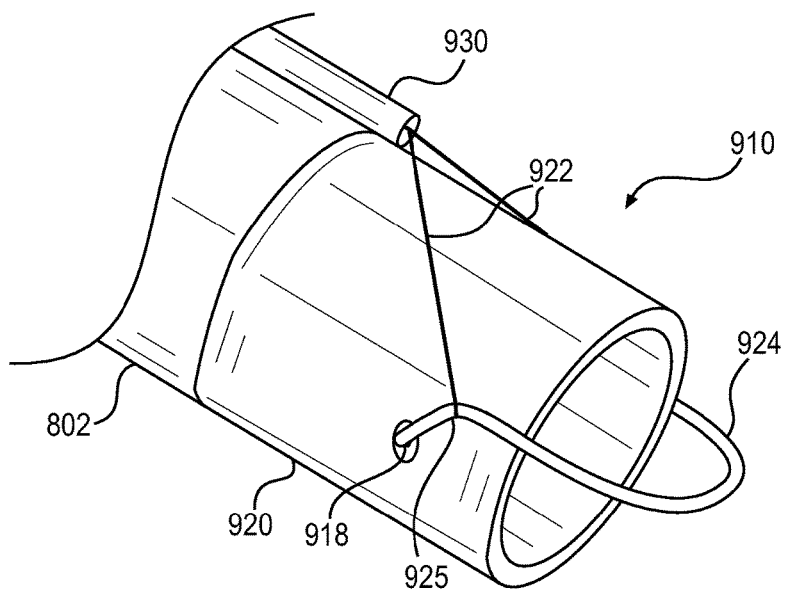
FIG. 9
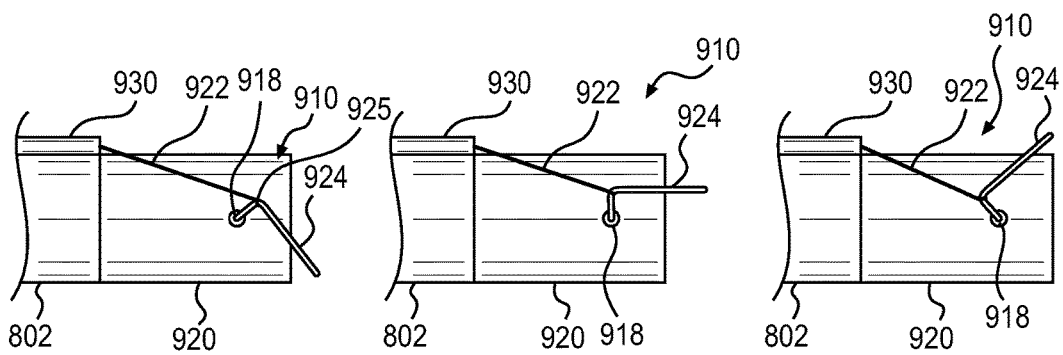
FIG. 10A   FIG. 10B   FIG. 10C

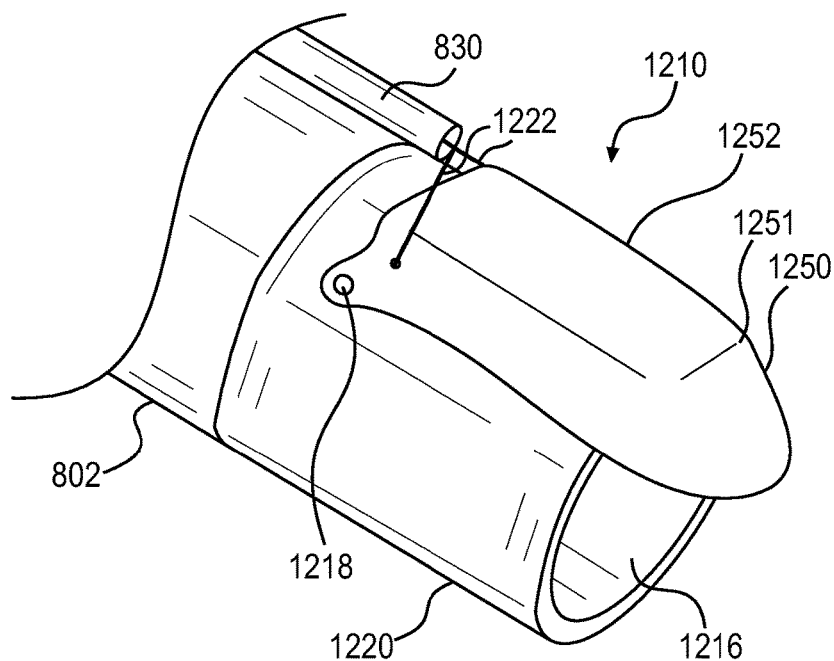
FIG. 12A
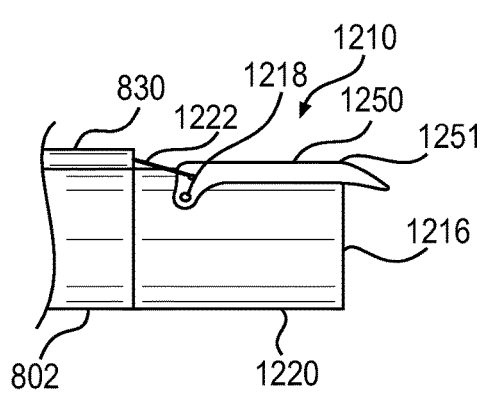 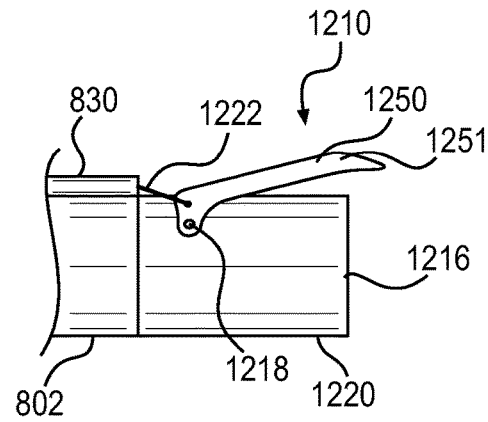
FIG. 12B    FIG. 12C

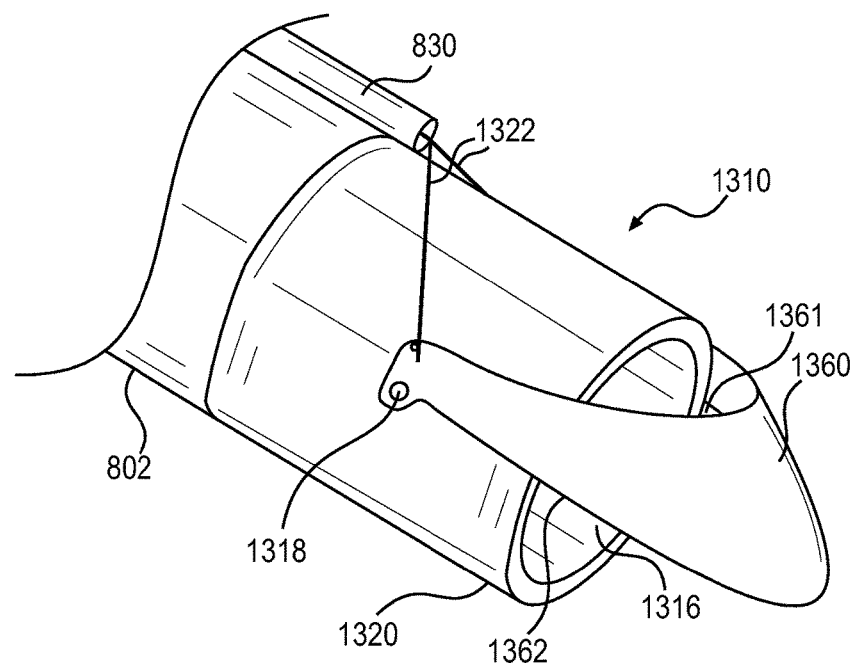
FIG. 13A
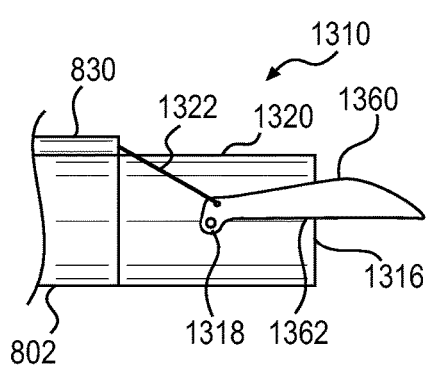
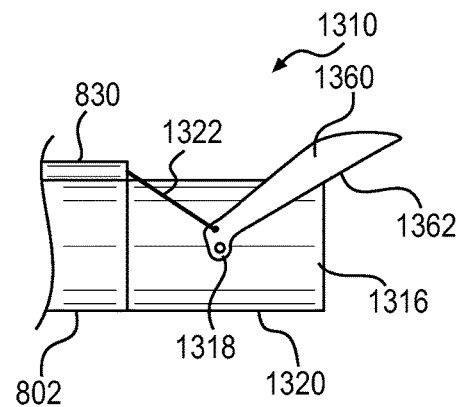
FIG. 13B    FIG. 13C

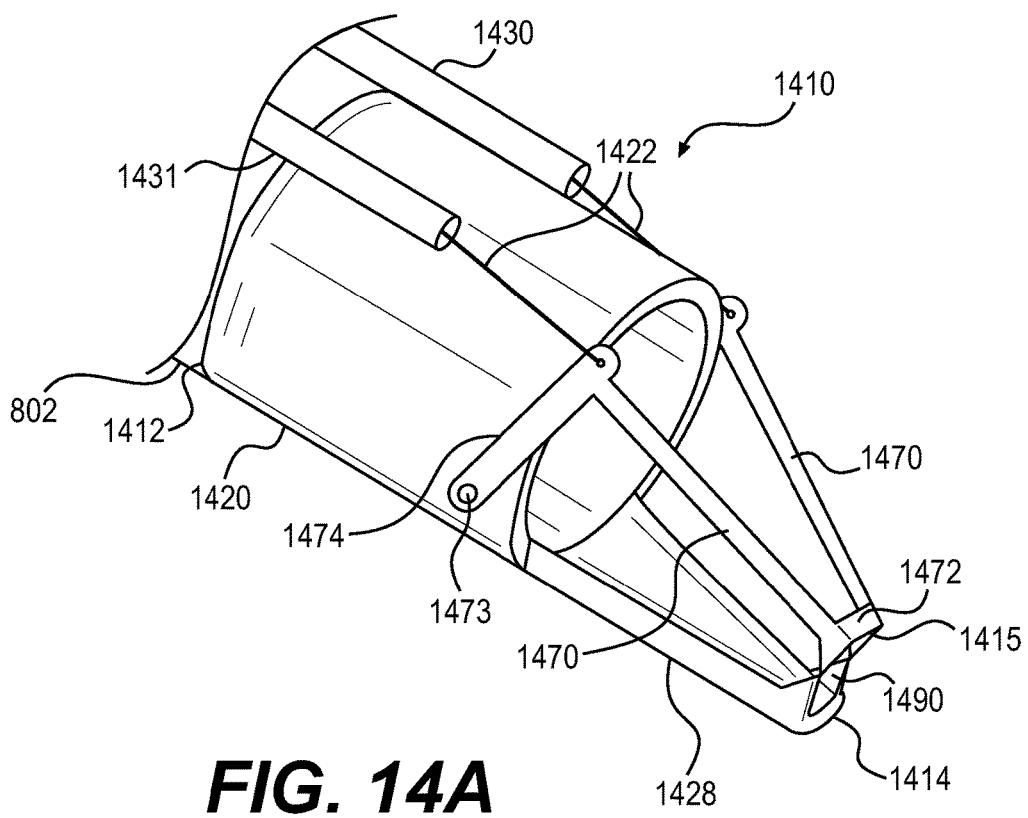
FIG. 14A
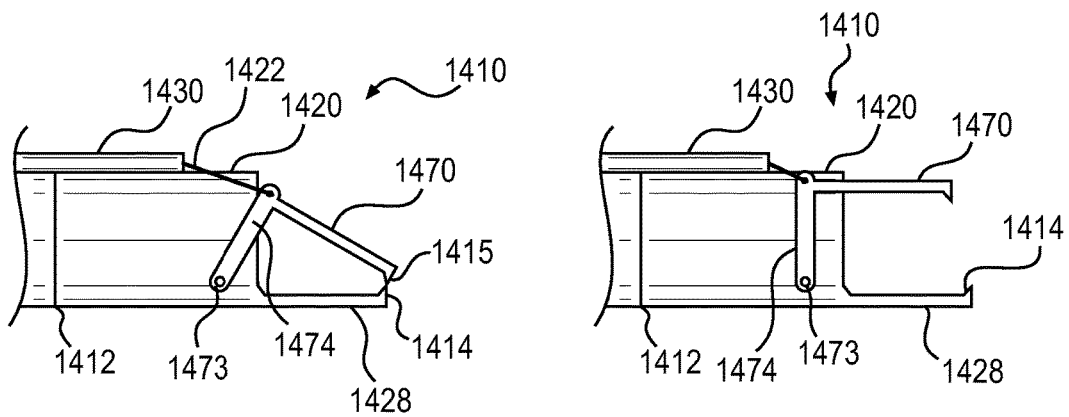
FIG. 14B     FIG. 14C

MEDICAL DEVICES AND RELATED METHODS OF USE

CROSS-REFERENCE TO RELATED APPLICATION

This application is a continuation-in-part application of U.S. application Ser. No. 13/774,719, filed Feb. 22, 2013, which claims the benefits of priority under 35 U.S.C. § 119 to U.S. Provisional Patent Application No. 61/602,372, filed Feb. 23, 2012, entitled EXPANDABLE ENDOSCOPIC HOODS AND RELATED METHODS OF USE, the entirety of all of the applications in this paragraph being incorporated herein by reference.

FIELD

This disclosure relates generally to devices and methods for dissecting and resecting tissue. More particularly, embodiments of the disclosure relate to minimally invasive devices and methods for endoscopic mucosal resection, endoscopic submucosal dissection, and per-oral endoscopic myotomy (POEM).

BACKGROUND

Organ walls are composed of several layers: the mucosa (the surface layer), the submucosa, the muscularis (muscle layer), and the serosa (connective tissue layer). In gastrointestinal, colonic, and esophageal cancer, e.g., small polyps or cancerous masses may form along the mucosa and often extend into the lumens of the organs. Conventionally, this condition is treated by cutting out a portion of the affected organ wall. This procedure, however, may cause discomfort to patients, and pose health risks. Recently, physicians have adopted a minimally invasive technique called endoscopic mucosal resection (EMR), and another called endoscopic submucosal dissection (ESD), which removes the cancerous or abnormal tissues (e.g., polyps), keeping the walls intact. EMR may also assist in removing any undesired tissue, even if such tissue is not abnormal or diseased. For purposes of this disclosure, the term "lesion" or "abnormality" includes, and will be used to refer to, these cancerous or abnormal tissues generally.

EMR and ESD are generally performed with an endoscope, which may be a long, narrow elongate member optionally equipped with a light, imaging device, and other instruments and defining a lumen extending from a proximal to a distal end of the elongate member. During ESD, the endoscope is passed down the throat or guided through the rectum to reach an undesired tissue, such as a polyp, in an affected organ. The distal end of the endoscope, typically equipped with a hood carrying dissecting tools such as a small wire loop, a band, or a knife is guided towards the undesired tissue. For EMR, the undesired tissue may be drawn into the hood. This may be achieved by applying suction through working channel extending along the lumen, or by retracting a retraction tool that is extendable from the endoscope. When the undesired tissue is sufficiently drawn into the hood, the dissecting tool may dissect portions of the tissue or resect target tissue from the organ wall. Subsequently, the excised tissue may be extracted for examination, biopsy, or disposal.

For ESD, the hood is typically used to create a working volume, applying tissue tension for endoscopic instruments, and preventing extraneous tissue and debris from interfering with the operator's visualization and operation.

Conventional endoscopic hoods may provide sufficient volume to operate on, e.g., small areas of target tissue (~smaller than 30 mm), but prove insufficient for dissecting, e.g., larger areas of target tissue (~larger than 30 mm). The volume offered by conventional hoods is not sufficient to effectively grasp and resect larger tissue area, such as, e.g., large lesions. As a result, certain large lesions may not be resected properly, forcing the operator to perform the procedure multiple times. Numerous attempts, along with increased operation time, increase the risk of damaging the submucosal wall and causing irreparable damage to the surrounding tissue.

SUMMARY

Embodiments of the present disclosure provide a device for resecting an undesired mass or otherwise unwanted tissue from a patient's body using a minimally invasive surgical method.

In accordance with an aspect of the present disclosure, a medical device may include an elongate member having a proximal end and a distal end. The distal end of the elongate member further includes a distal portion defining an end face and a cavity extending distally there from. The distal portion further including a plurality of sections configured to transition between a first position and a second position different than the first position. Further, a mechanism may be configured to adjust a volume of the cavity to, e.g., allow for resection of larger tissue volumes, by moving at least one of the plurality of sections from the first position to the second position. In other instances, the embodiments disclosed herein may be used to separate tissue layers along natural intersections. For example, the embodiments of FIGS. 3A-3B may be used for tunneling and separating the muscularis layer from the mucosal layer. The hood may be used as blunt plow-like device, or may be opened to force the layers apart. Further, the embodiments disclosed herein may be used to place tissue under tension to, e.g., assist in cutting the tissue.

In various embodiments, the device may include one or more of the following features: the distal portion may be removably coupled to elongate member; the plurality of sections may include two sections; the plurality of sections may include four sections; the cavity may include a distally-facing opening; at least one of the plurality of sections may be biased towards the first position; the elongate member may further include a plurality of channels extending between the proximal and distal ends; a tissue cutting device may be disposed in one of the plurality of channels; and at least one of the plurality of sections may include edges configured to cut through tissue. Further, the devices disclosed herein may be shaped (e.g., tapered or pointed) to aid in delivery through tissues or tight spaces. That is, the devices disclosed herein may include a leading nose to assist in delivery.

In accordance with another aspect of the invention, a medical device may include an elongate member having a proximal end, a distal end, and a lumen extending therebetween. The distal end may define an end face of the elongate member. The medical device further includes a hood having a proximal end and a distal end, such that the proximal end is configured to receive the distal end of the elongate member. Further, a distal portion of the hood includes a plurality of sections configured to transition between a closed state and an open state, the plurality of sections defining a cavity extending distally from the end face of the elongate member.

In various embodiments, the device may include one or more of the following features: the hood may include a flexible material and the plurality of sections may be formed by slits introduced in the flexible material; the plurality of sections may include four sections; wherein, when the plurality of sections are in the open state, the cavity may include a distally-facing opening; wherein, when the plurality of sections are in the closed state, the cavity does not include a distally-facing opening; and wherein transitioning the plurality of sections from the closed state to the open state increases a dimension of the cavity. Further, the hoods disclosed herein may include a lubricious material, coating, or surface geometry.

In accordance with yet another aspect of the invention, a medical device may include an elongate member having a proximal end, a distal end, and a lumen extending therebetween. The distal end defines an end face of the elongate member. The medical device further includes a hood including a proximal end and a distal end. A distal portion of the hood includes a plurality of sections configured to transition between a closed state and an open state. The plurality of sections may define a cavity extending distally from the end face of the elongate member. The device may further include a sheath including a proximal end, a distal end, and one or more channels extending therebetween. The sheath may be configured to slidably receive the hood within one of the channels. The hood may be configured to transition between the closed state while in the channel of the sheath and the open state while out of the channel.

In various embodiments, the device may include one or more of the following features: the plurality of sections may be made integrally with one another; the plurality of sections may be biased towards the open state; and a device configured to sever tissue.

According to another aspect of the present disclosure, a tissue retractor for attachment to an elongate member of a medical device may include a cap having a central longitudinal axis and an actuator connected to the moveable component to transition the moveable component across the central longitudinal axis from an insertion state to an actuated state. The cap may include an attachment section adapted to attach to a distal end of the elongate member and a moveable component pivotally attached to the attachment section at one or more pivot points.

Additionally or alternatively, the tissue retractor may include one or more other features describe here. For example, when in the insertion state, the moveable component may be configured to be inserted into a patient's body and between a first layer of tissue and a second layer of tissue. In another example, when in the actuated state, the moveable component may be configured to move the first layer of tissue away from the second layer of tissue. The cap may include a stationary portion contacting the moveable component at a distal end of the cap, the stationary portion may be configured to remain stationary relative to the attachment section when the moveable component transitions from the insertion state to the actuated state. The stationary portion may taper from a proximal end of the stationary portion to a distal end of the stationary portion. The moveable components may include a first portion and a second portion, and the first portion may be approximately perpendicular to the second portion. The moveable component may include a gap for a tool to extend through and distally of the moveable component. The cap may be removably attached to the elongate member. The tissue retractor may include a biasing member configured to bias the moveable component in the insertion state.

According to another aspect of the present disclosure, tissue retractor for attachment to an elongate member of a medical device. The tissue retractor may include a cap having a central longitudinal axis. The cap may include an attachment section adapted to attach to a distal end of the elongate member, a stationary component having a distal end, a moveable component pivotally attached to the attachment section at one or more pivot points; wherein, when in an insertion state, a distal end of the moveable component mates with the distal end of the stationary component. The tissue retractor may further include an actuator connected to the moveable component to pivot the moveable component away from the stationary component to transition the moveable component from the insertion state to an actuated state.

Additionally or alternatively, the tissue retractor may include one or more other features describe here. For example, when in the insertion state, the moveable component may be configured to be inserted into a patient's body and between a first layer of tissue and a second layer of tissue. When in the actuated state, the moveable component may be configured to move the first layer of tissue away from the second layer of tissue. The stationary portion may taper from a proximal end of the stationary portion to a distal end of the stationary portion. The moveable component may include a gap for a tool to extend through and distally of the moveable component. The cap may be removably attached to the elongate member. At least a portion of the moveable component may be a bar, and the bar may pivot across the central longitudinal axis. The moveable component may include a first portion and a second portion, and the first portion may be approximately perpendicular to the second portion. When in the insertion state, the moveable component may contact the stationary component. When in the actuated state, the second portion may contact the attachment.

According to another aspect of the present disclosure, a method of retracting tissue may include inserting a cap into a body. The cap may have a central longitudinal axis and includes a moveable component and an attachment section. The method may also include inserting the moveable component between a first layer of tissue and a second layer of tissue, and actuating an actuation mechanism proximally to rotate the moveable component across the central longitudinal axis to lift the first layer of tissue away from the second layer.

Additionally or alternatively, the method may include one or more other features described here. The cap may include a stationary portion, and, during the step of actuating the actuation mechanism, the moveable component may rotate away from the stationary portion. Prior to the step of actuating the actuation mechanism, the moveable component may contact the stationary portion. The method may further include inserting the stationary portion between the first layer of tissue and the second layer of tissue. The method may include removably attaching the cap to an elongate member of a medical device.

Additional objects and advantages of the instant disclosure will be set forth in part in the description, which follows, and in part will be obvious from the description, or may be learned by practice of the present disclosure. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 9 is perspective distal end view of an alternative exemplary endoscopic cap, according to another embodiment of the present disclosure.

FIGS. 10A, 10B, and 10C are side views of the endoscopic cap of FIG. 9 in unactuated and actuated states, according to another embodiment of the present disclosure.

FIGS. 12A, 12B, and 12C are perspective and side views of an alternative exemplary endoscopic cap in unactuated and actuated states, according to another embodiment of the present disclosure.

FIGS. 13A, 13B, and 13C are perspective and side views of an alternative exemplary endoscopic cap in unactuated and actuated states, according to another embodiment of the present disclosure.

FIGS. 14A, 14B, and 14C are perspective and side views of an alternative exemplary endoscopic cap in unactuated and actuated states, according to another embodiment of the present disclosure.

DESCRIPTION OF THE EMBODIMENTS

Figure 1:
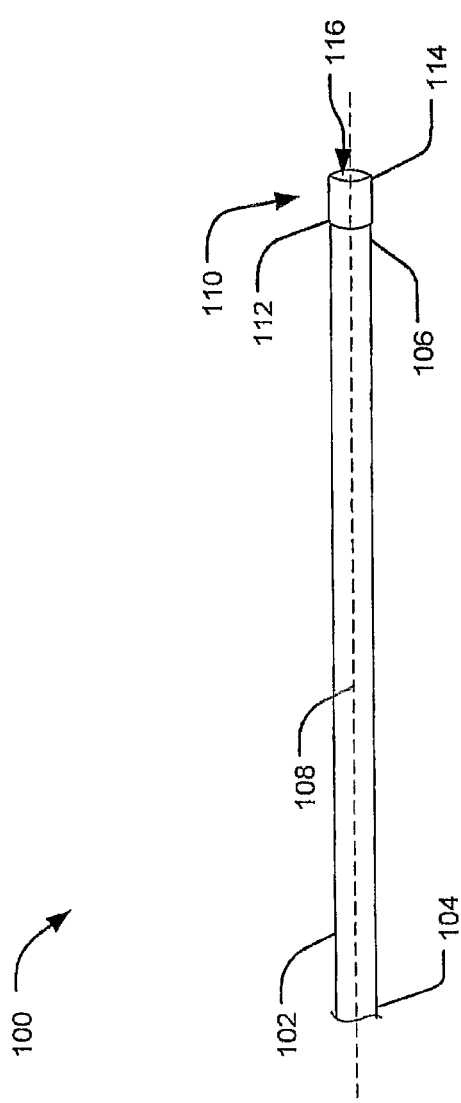
FIG. 1 is a side view of an exemplary endoscopic resection device, according to an embodiment of the present disclosure.

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient. When used herein, the terms "approximately" and "substantially" may indicate a range of values within +/−5% of a stated value.

Overview

Embodiments of the present disclosure relate to devices and methods for moving through tissues, manipulating tissues, making space (for procedures) within tissues, and dissecting or resecting undesired tissue (e.g., cancerous lesions and/or polyps) from within a patient's body. For example, the device may be used in a minimally invasive procedure to remove cancerous polyps or lesions from the mucosal walls of the colon, esophagus, stomach, duodenum, or any other suitable location. In fact, those of ordinary skill will readily recognize that the principles of the present disclosure may be used to remove target tissue from any location within a patient's body, regardless of whether the target tissue is abnormal or diseased. A physician may also wish to resect tissue to conduct a biopsy or other examination. It should be understood that the resection device may perform the functions of dissecting, transecting, resecting, retrieving, or another medical procedure, but for convenience, the term "resection device" will be used throughout this application.

For conducting such procedures, embodiments of the resection device described in this disclosure include an ESD, EMR, and/or POEM hood assembly coupled to a distal portion of any suitable elongate member or other introduction sheath, such as an endoscope, that is operable to create a working volume that is approximately the size of the tissue area targeted for removal. To this end, the hood may be expandable to increase its working volume according to the size of the targeted tissue area. The present disclosure illustrates various embodiments of an expandable hood, in accordance with the present disclosure. It will be understood, however, that these embodiments are not exhaustive and that many other configurations are conceivable and within the scope of the present disclosure.

In the following sections, embodiments of the present disclosure will be described using an exemplary body organ—the gastrointestinal tract. The embodiments of the resection device aim effectively to dissect and/or remove desired tissue, such as, e.g., lesion on an inner wall of the stomach, without damaging the underlying tissue layers. It will be understood that the stomach is merely exemplary, and that the device may be utilized in any other suitable organ, including the gastrointestinal tract, such as the colon, duodenum, esophagus, or any other organ where tissue removal may be desired. In addition, it will be understood that the principles of the present disclosure may be used to remove other objects such as, e.g., kidney or biliary stones, previously placed implants, or any other desired masses from within a patient's body.

Exemplary Embodiments

FIG. 1 is a side view of one embodiment of a resection device 100 of the present disclosure for dissecting and/or resecting polyps, lesions, or other undesired tissue from the interior bodily walls of a patient. Resection device 100 includes an elongate member 102 having a proximal end 104, a distal end 106, and a lumen 108 extending between proximal and distal ends 104, 106. Proximal end 104 may be coupled to a handle (not shown), while distal end 106 may be permanently or removably coupled to a hood 110. In some embodiments, hood 110 may be made integrally with distal end 106.

Elongate member 102 may be any flexible or rigid member adapted to be inserted into a patient. Further, elongate member 102 may be flexible in certain portions and rigid in others. For example, the elongate member's distal end 106 may be flexible or steerable, allowing the member to traverse circuitous cavities or lumens, while the rest of the member may be rigid to allow the elongate member 102 to be inserted into a body cavity.

In the illustrated device, elongate member 102 has a generally circular cross-section, with a generally circular hollow interior lumen 108, although not so limited in various embodiments. Indeed, elongate member 102 and lumen may have any suitable cross-section geometries, including, e.g., rectangular and/or ovular. Further, elongate member 102 may have a uniform diameter or may be tapered at the distal end 106 to facilitate insertion into a patient's body. Depending upon the particular implementation and intended use, the length and configuration of elongate member 102 may vary.

Lumen 108 may include one or more channels (not shown). Through these channels, an operator may introduce one or more medical devices to extend out of the distal end 106. For example, during a resectomy, the operator may introduce a suction device into one channel and a snare loop into another. Additionally, from time to time, during a procedure, the operator may introduce a light source, a camera, an injector, or a morcellator into one or more of the other channels. Because different implements may need to be inserted into the elongate member 102, the dimensions of its channels may vary. Some channels may have a larger diameter, while others may have a smaller diameter. Further, some channels may include permanently fixed medical devices, such as light sources or imaging devices, while other channels may allow temporary insertion and removal of medical devices, as the operator desires.

The elongate member 102 may be coated with lubricious materials and antibacterial agents to ease insertion into tight cavities and prevent infections, respectively. In addition, elongate member 102 may comprise lubricious materials or surface designs. Further, portions of the elongate member 102 may include radiopaque materials to visualize the position of elongate member 102 within a patient's body. Elongated member 102 described here may be any well-known endoscopic device used for colonoscopy, resectoscopy, cholangioscopy, or mucosal resection, and thus, this device will not be discussed in detail in the remainder of the disclosure.

Hood 110 may be a generally tubular elongated member configured to be secured to the elongated member's distal end 106. In the depicted embodiment, for example, hood 110 may include a proximal portion configured to fit over distal end 106. Alternatively, hood 110 may be configured to fit into and extend from a lumen of elongated member 102. The hood 110 has a proximal end 112, a distal end 114, and a lumen 116 extending from the hood's proximal end 112 to the hood's distal end 114. The hood may further include a mechanism allowing it to transition between two states: a first state, in which the hood is closed or has a reduced diameter and an expanded state, in which at least a distal portion of the hood is expanded radially. The diameter of the hood in its first state may, for instance, be similar to that of the elongate member 102. The expansion mechanism may include pull wires, elongate tubes, springs, levers, pulleys, or other mechanisms for reconfiguring the hood to the expanded state.

Hood 110 may be temporarily or permanently attached to the elongate member's distal end 106. By configuring the hood to complementarily engage with the distal end of a conventional endoscope or catheter, the hood can be used with existing endoscopes and catheters. A permanently attached hood ensures that hood 110 does not inadvertently separate from the elongate member's distal end 106 during a procedure. On the other hand, however, a removably coupled hood may allow for utilizing hoods of differing sizes. Based on the desired application, hoods may be manufactured either permanently attached to the distal end of elongate member 102 or with attachment means to temporarily attach the hoods 110 to elongate members 102 having complementary attachment means.

For temporary attachment, the proximal portion of the hood may include a substantially open attachment section, e.g., cylindrical, defining a recess for receiving a distal end of elongate member 102. The recess may include threading, projections, grooves, or any other temporary attachment means for attaching the hood to complementary structures on the elongate member. Thus, temporary attachments may, for instance, be defined by a screw-fit, Luer taper, snap-fit, or compression fit arrangement. In some embodiments, the attachment section may be adjustable, allowing operators to connect elongate members of varying configurations or sizes to the hood. For instance, the attachment section may be formed of a flexible material, such as elastic, or rubber, which may expand radially to allow the hood to fit over a range of elongate members with diameters greater than that of the hood's attachment section. It will be understood that the attachment section can be made from different materials and be configured differently to provide for adjustability without departing from the scope of the present disclosure. Furthermore, mechanisms for holding the attachment section to the endoscope may be used, including, e.g., hose clamps, wrapped filaments, clips, etc.

Permanent attachment may include welding, gluing, soldering, or other forms of attachment, or the hood 110 may be integrally formed with elongate member 102. It will be appreciated that other forms of temporary or permanent attachment may be adopted without departing from the scope of the present disclosure. In some embodiments, hood 110 may be integral with a sheath which fits along a portion of the endoscope from the distal end and proximally. In further embodiments, this sheath may extend substantially the entire length of the endoscope.

Hood 110 may be formed of any suitable biocompatible material, such as polyurethane, plastics, polymers, and metals including shape memory or superelastic materials for instance, Nitinol.

The hood 110 may also be coated with antibacterial and/or lubricious agents that prevent bacterial infections and/or allow the hood to easily pass through the lumens and cavities within a patient's body with minimal or no abrasion or bruising to surrounding tissue. Hood 110 may also comprise a lubricious material or surface, and/or surface designs that facilitate ease of insertion.

In the following sections, with reference to FIGS. 2-7, various exemplary embodiments of an expandable hood are described.

Figure 2A:
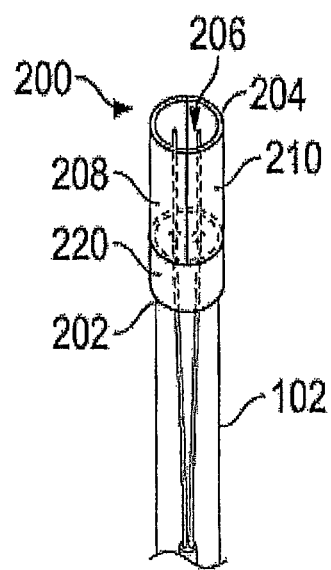
FIGS. 2A and 2B are perspective distal end views of an exemplary endoscopic hood in closed and expanded states, respectively, according to an embodiment of the present disclosure.
Figure 2B:
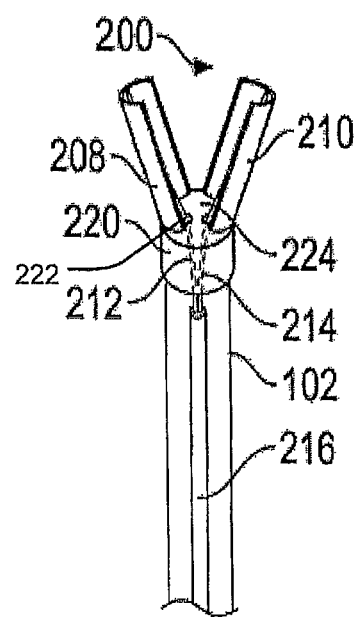

FIGS. 2A-2B is a perspective distal end views of an exemplary endoscopic hood 200 according to an embodiment of the present disclosure. More particularly, FIG. 2A illustrates hood 200 in a closed state and FIG. 2B illustrates the hood 200 in an open or expanded state. Here, as previously described, hood 200 includes a substantially tubular structure extending from a proximal end 202 to a distal end 204, and defines a lumen 206 extending from a proximal end 202 to a distal end 204. In the closed position, lumen 206 may define a working volume of the hood 200. Hood 200 in this embodiment takes the form of a hollow cylinder bisected into two substantially equal semi-cylindrical sections 208, 210 along a longitudinal axis. In some embodiments, the bisection is off-center, creating one section which is longer than the other. One advantage of such an embodiment may be to create a smaller leading distal tip on the hood. In the closed state, the two sections 208, 210 abut each other to form a circular distal opening, as shown in FIG. 2A. In the expanded state, the two sections 208, 210 may expand to increase the effective working volume of hood 200. In some embodiments, only one of sections 208, 210 may move relative to the other of sections 208, 210.

A portion, e.g., the proximal or distal ends, of each section 208, 210 maybe coupled to pull wires 212, 214. Although the depicted embodiments illustrate two pull wires 212, 214, some embodiments may include more or less (e.g., only one pull wire) pull wires. Further, a proximal portion of each of the two sections 208, 210 may be connected by means of hinges to a cylindrical attachment section 220, which connects the hood to the distal end of the elongate member 102. The hinge(s) may be a living hinge if each section is connected to the other toward a proximal end of hood 200. In another embodiment the sections 208, 210 may be coupled directly to the elongate member 102. The pull wires 212, 214 extend down the lumen of the elongate member 102 and are configured to be operable by a user at the proximal end of the elongate member 102 to move the sections 208, 210 between a closed state and an open state. In some embodiments, each of sections 208, 210 of hood 200 may be controlled independently. That is, each of sections 208, 210 may open or close independent of the other.

Depending on the points of attachment of the pull wires 212, 214 to the sections 208, 210, a tensile force on the wires will either close or open (expand) the hood. The pull wires 212, 214 may be sufficiently rigid to allow a compressive force to be transmitted to the sections 208, 210 to open or close the hood. Furthermore, the sections 208, 210 may be spring loaded or otherwise biased to remain in a normally open or normally closed position such that tensile force on the pull wires 212, 214 serves to close or open the hood against the natural bias. In other embodiments, an elastic band, e.g., may wrap around a portion of hood 200 to bias it to the closed position. In the embodiment of FIGS. 2A-2B, the pull wires 212, 214 are connected to points 222, 224, respectively. Thus, in order to keep the hood in the closed state (FIG. 2A), the pull wires are pulled at their proximal ends. In order to allow the hood to adopt its expanded configuration, the tensile force applied to the wires is released, allowing the sections 208, 210 to swing open.

The pull wires 212, 214 may be slidably mounted in a sheath 216, or two separate sheaths (not shown). Sheath 216, in one embodiment, is secured to the outer surface of elongate member 102 and extends from proximal end 202 of the hood 200 to the proximal end of elongate member 102. Any known securing means, such as retaining bands, clips, or fasteners, may be utilized to ensure that sheath 216 does not separate from the elongate member during operation. Alternatively, the sheath 216 may be present within the lumen of elongate member 102.

In other embodiments, pull wires 212, 214 may be mounted to run through one of the working channels of the elongate member 102 from the distal end to the proximal end of the elongate member 102, or one or more wire-supporting channels for supporting the pull wires may be formed into the walls of the elongate member 102. In yet another embodiment, sheath 216 may simply be secured to an inner wall of the elongate member using any known securing mechanism. It will be understood that other embodiments may be contemplated regarding the placement of pull wires relative to the elongate member 102, and none of these embodiments are outside the scope of the present disclosure.

In the embodiment shown in FIGS. 2A-2B, hood 200 may be substantially cylindrical in the closed state, having a circular distal opening. In other embodiments, however, the hood's shape may vary considerably. For example, the hood may have a conical, semi-elliptical, semi-circular, or pyramidal shape without departing from the scope of the present disclosure. In addition, a distal portion of hood 200 may include a raised portion, such as, e.g., a lip to allow better contact during vacuum application. The lip may include any suitable configuration and may be softer and/or wider than the remainder of hood 200.

Furthermore, in some embodiments, a proximal end portion of hood 200 may be hinged to allow the proximal end of the hood 200 to expand along with the distal end. For example, if a scissor arrangement of links is provided as a proximal hinge, the proximal end of the hood 200 may expand wider than the distal end.

Figure 3A:
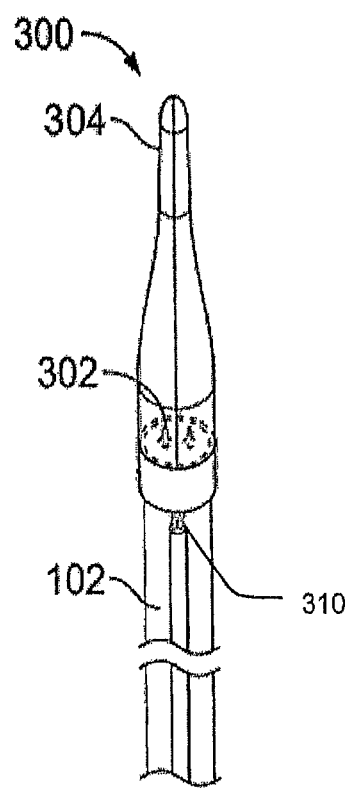
FIGS. 3A and 3B are perspective distal end views of an endoscopic hood in closed and expanded states, respectively, according to another embodiment of the present disclosure.
Figure 3B:
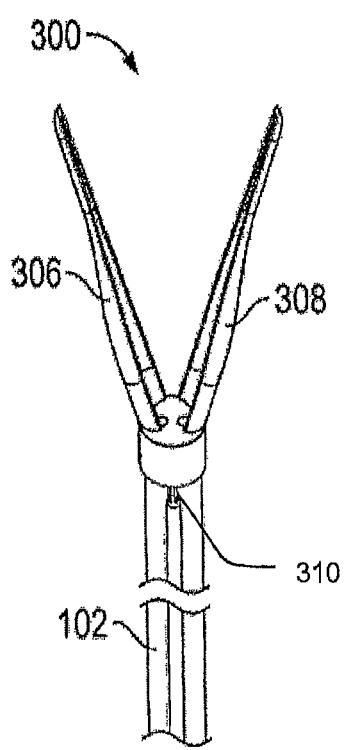

FIGS. 3A-3B depict end views of another exemplary hood 300, with FIG. 3A showing the hood 300 in a closed position and FIG. 3B showing hood 300 in an open or expanded position. Hood 300 extends from a proximal end 302 to a distal end 304, and may include one or more features of the other hood embodiments described herein, including those specifically described above with respect to FIGS. 2A-2B. Hood 300 may be shaped as a "duckbill," instead of a cylinder. Again, similar to the hood illustrated in FIGS. 2A-2B, the duckbill hood may be bisected longitudinally into two equal sections 306, 308. In this embodiment, the sections 306, 308 are pivotally connected directly to the distal end of elongate member 102, but could again be connected to an attachment section that secured the hood 300 to a distal end of elongate member 102.

Each section 306, 308 of the duckbill hood includes a proximal end 302 having diameter substantially similar to the elongate member's distal diameter. The distal ends of the sections 306, 308 taper such that when the two sections contact each other, there is no distal end opening. Outer surfaces of each section 306, 308 may include atraumatic configurations to eliminate the presence of any sharp edges or corners. Such a hood configuration may allow a user to grasp and securely retain therein, e.g., unwanted tissue or the like. In addition, when the duckbill hood 300 is in the closed position (see, e.g., FIG. 3A), the distal end 304 may be inserted in between two tissue portions and the hood may be opened to separate those tissue portions.

Sections 306, 308 transition from an expanded state to closed state using known mechanisms. In one embodiment, pull wires 310 extend from the proximal end of sections 306, 308 to a handle (not shown) operable by a user to move the sections 306, 308. Sections 306, 308 may assume their closed state by pulling the pull wires 310. By providing fairly rigid pull wires 310 that can support compressive forces, the pull wires 310 can also be used to open the hood 300 by pushing the pull wires.

In certain circumstances, the hood 300 may have to exert a radially outward force on the surrounding tissue in order to expand. For instance, in small cavities where large lesions are to be resected, hood 300 may not expand unless substantial radial force is exerted on the sections of the hood 300. Accordingly, the hood 300 may include some mechanism to exert this force. As discussed above, in some cases, the pull wires 310 may be rigid enough to provide the required force. In other embodiments, the hinged connection between the hood 300 and the elongate member 102 may include spring elements or certain groove and projection assemblies and pull wire connections that are configured to urge the sections of the hood 300 apart when a tensile force is exerted on the pull wires 310. In still further embodiments, sections 306, 308 may be biased either toward or away from one another.

For instance, in both the hood configurations illustrated in FIGS. 2A-2B and 3A-3B, the pull wires 310 may be attached to the distal ends of the hood sections instead of the proximal ends. To this end, the pull wires 310 may be coupled to the outer surface of the sections. Proximally pulling the pull wires 310 would then expand the hood 300 and distally pushing the pull wires 310 would urge the sections together to allow the hood 300 to assume its closed state. Other pull wire attachment locations may also be considered, such as centers, proximal portions, or distal portions of the sections, without departing from the scope of the present disclosure. In some embodiments, the distal end of the pull wires 310 may comprise a larger surface area than the body of the pull wires 310, e.g., by flattening the distal end. An increased surface area may increase the attachment strength of the pull wires 310 to the hood 300.

The duckbill configuration of hood 300 allows it to be wedged into small gaps of incisions so that the expanding action may dissect tissue in a blunt fashion along, e.g., natural tissue interfaces. As described previously other hood configurations may be also used.

Figure 4A:
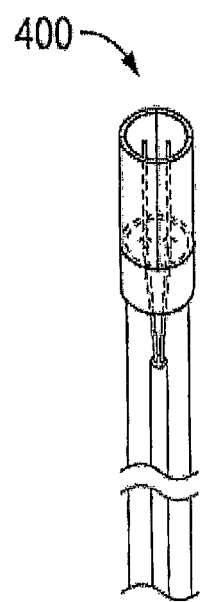
FIGS. 4A and 4B are perspective distal end views of an endoscopic hood in closed and expanded states, respectively, according to a further embodiment of the present disclosure.
Figure 4B:
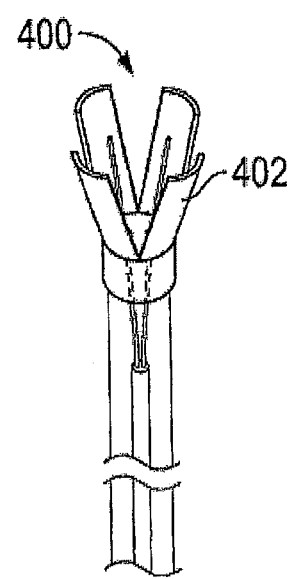

FIGS. 2A-2B and 3A-3B illustrate different configurations of hood embodiments, but in both of these configurations, the disclosed hood is essentially bisected into two sections. FIG. 4A is a perspective dimensional view of another embodiment of a hood 400 in the closed state and FIG. 4B shows the hood 400 in an expanded state. Here, the hood 400 includes more than two sections. In particular, this embodiment shows a hood comprising four sections, which come together to form a cylindrical shape member having a circular distal opening. In each of the embodiments described above, the hood is divided into two or more sections that assume a closed state and an expanded state. In the expanded state, the sections of the hood diverge from each other to increase the working volume of the hood. In the closed state, however, various sections of the hood come together to form a closed volume, which may either have a distal opening, shown in FIG. 2A, or the hood may be completely closed from its distal end, as shown in FIG. 3A.

Various alternatives of the hood 200 or 300 may be contemplated. It will be appreciated that the hood may include a greater or lesser number of sections without departing from the scope of the present disclosure. Four sections distribute the retraction force better than two sections and create a larger and more circular working volume. Even so, the present disclosure contemplates embodiments having two, three, or more sections. As in the embodiments discussed with respect to FIGS. 3A-3B and 4A-4B, the pull wires in this embodiment are coupled to the proximal ends of the sections but could again be attached to the distal ends of the sections or any portion along the length of the sections. Further, the illustrated embodiment has a cylindrical shape. Other shapes may however be implemented using more than two sections. For example, the duckbill hood may include four sections. Additionally, the plurality of sections may be connected by a flexible membrane (not shown) to allow for suction to the chamber when in the open position.

Figures 5A, 5B:
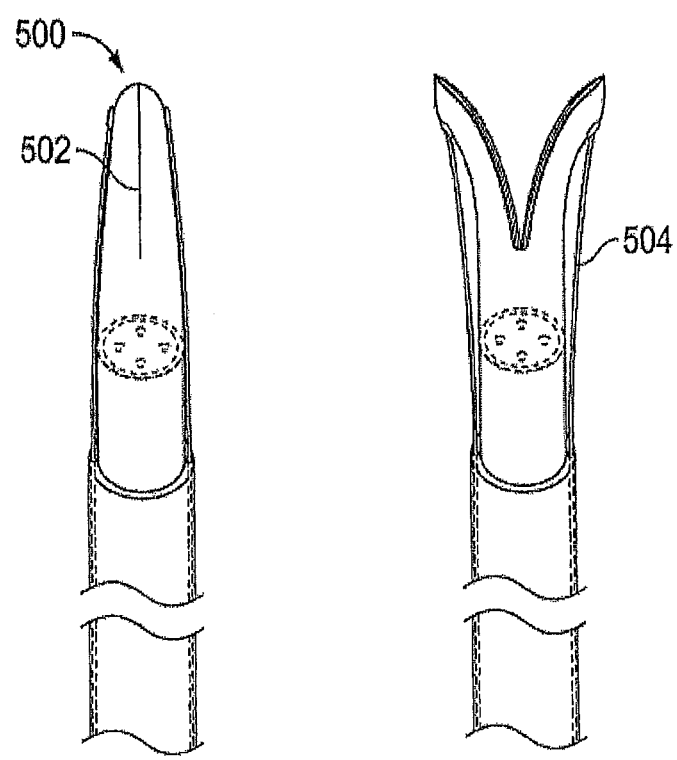
FIGS. 5A and 5B are perspective distal end views of an endoscopic hood in closed and expanded states, respectively, according to another embodiment of the present disclosure.

FIGS. 5A-5B are perspective views of yet another embodiment of a hood 500. FIG. 5A shows the hood 500 in a closed state and FIG. 5B shows the hood 500 in an open or expanded state. Here, instead of hinged sections, the hood 500 is made of a flexible material. A slit 502 is introduced in a distal portion of hood 500. As shown, for example, slit 502 may extend proximally from a distal end of hood 500 to a location distal of the proximal end of hood 500. Pull wires 504, attached to the outside distal portion of the hood 500 the elongate member exert a force on the distal end of the hood when pulled at the proximal end of the elongate member, thereby widening the slit 502 and expanding hood 500. In the closed state, however, the slit 502 is narrowed such that hood 500 remains completely closed from its distal end with no distal opening, as shown in FIG. 5A.

The hood 500 may be made of any suitable, substantially flexible material such as a plastic, polymer, elastomer, etc. Further, edges of the distal end of hood 500 may be sharpened or include cautery capabilities for tissue resection.

While the embodiment shown in FIG. 5 includes only one slit 502, more silts may be introduced in the distal end of the hood. It will be understood that the number of pull wires attached to hood 500 will vary based on the number of slits. For example, in case of one slit, two pull wires may be provided, while for two slits, four pull wires are preferably provided.

Further, the shape of hood may vary based on the desired application. In some cases, the hood may have a hollow cylindrical configuration, while in others, the hood may have a substantially dome shaped, duckbill shaped, conical, pyramidal, elliptical, or other shaped distal portion without departing from the scope of the present disclosure. In addition, the pull wires in the configuration of FIG. 5 may be attached to the inner distal surfaces of the hood. Distally pushing the pull wires, in such a scenario may expand the hood, increasing its volume.

Figures 6A, 6B, 6C:
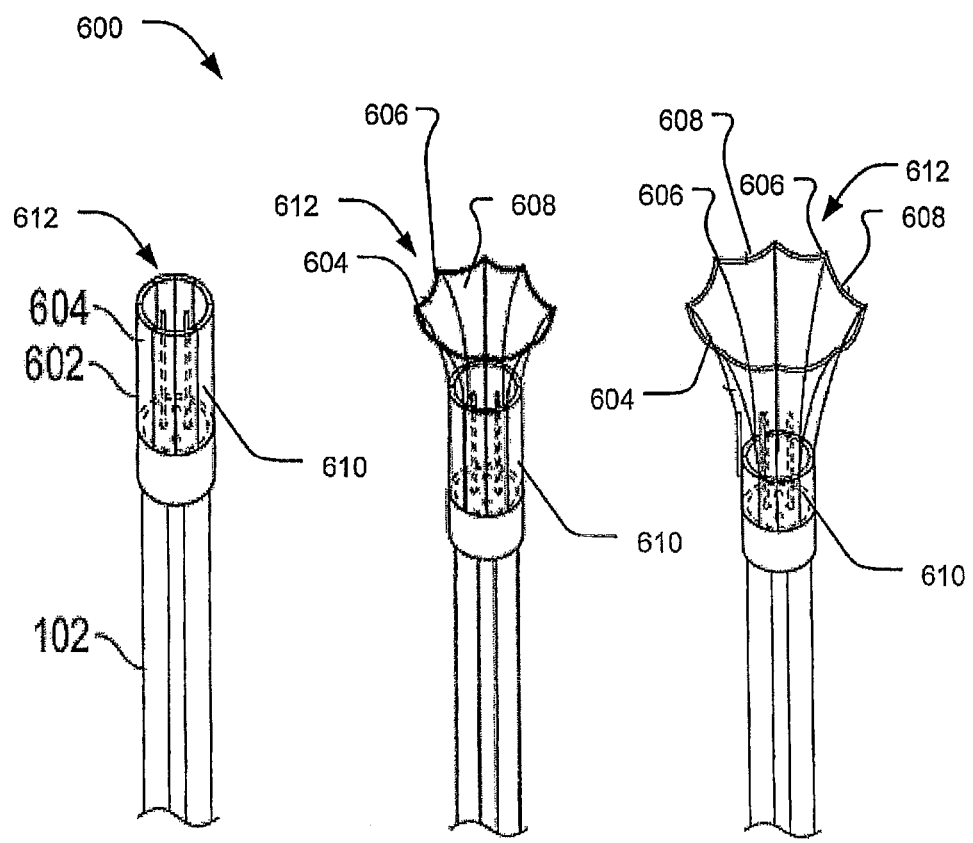
FIGS. 6A, 6B, and 6C are perspective distal end views of an endoscopic hood in different states of expansion, according to an even further embodiment of the present disclosure.

FIGS. 6A-6C are perspective views showing three positions of yet another embodiment of a hood of the present disclosure. As noted above, any embodiment disclosed herein may include one or more features described in connection with any of the other embodiments described herein. In the first position (FIG. 6A), hood 600 is in the closed state; in the second position (FIG. 6B), hood 600 is partially expanded; and in the third position (FIG. 6C), hood 600 is in an expanded state. Hood 600 includes a sheath 602, and an expandable hood portion 604 slidably mounted within a lumen 610 defined by the sheath 602. In the closed position, lumen 610 may define a working volume of the hood 600. Hood 600 takes the form of a hollow cylinder having expandable hood portion 604, which is divided into substantially equal sections along a longitudinal axis. In the closed state, the sections of hood portion 604 abut each other to form a closed cylinder having a circular distal opening, as shown in FIG. 6A. In the expanded state, however, the sections of hood portion 604 may expand to increase the effective working volume of hood 600.

In the embodiment shown, the sheath 602 extends over a distal portion 106 of the elongate member 102. In another embodiment (not shown), the sheath 602 may run along the entire outer surface of the elongate member 102. In yet another embodiment (not shown), sheath 602 may run along a portion or the entire length of the elongate member's inner surface.

Sheath 602 may be any flexible or rigid member adapted to include expandable hood portion 604 at its distal end. Further, sheath 602 may be flexible in certain portions and rigid in others. For example, the sheath's distal end may be flexible or steerable, allowing the hood 600 to traverse circuitous cavities or lumens.

In the illustrated device, sheath 602 has a generally circular cross-section, with a generally circular hollow interior lumen 610. Depending upon the particular implementation and intended use, the length and configuration of sheath 602 may vary.

Lumen 610 may include one or more channels (not shown). Through these channels, an operator may introduce one or more medical devices to extend out of the distal end 612. For example, the hood 600 may extend from one channel and other medical tools required for resection, visualization, may be introduced through other channels of the lumen 610.

The sheath 602 may be coated with lubricious materials and antibacterial agents to ease insertion into tight cavities and prevent infections, respectively. Further, portions of the sheath 602 may include radiopaque materials to visualize the position of sheath 602 within a patient's body. Sheath 602 described here may be any well-known endoscopic device used for colonoscopy, resectoscopy, cholangioscopy, or mucosal resection, and thus, this device will not be discussed in detail in the remainder of the disclosure.

In the embodiment of FIGS. 6A-6C, the expandable hood portion 604 is moveable between a closed state, within the sheath 602 and an open or expanded state in which it extends from the distal end of sheath 602. The expandable hood portion 604 includes urging means that urge the expandable hood portion 604 to expand outwardly in funnel-like fashion when not constrained by the sheath 602. In this embodiment, the urging means comprises multiple, substantially equidistant pull wires 606 encased in a flexible membrane 608. The illustrated embodiment includes six wires, but a greater or lesser number of wires may be used without departing from the scope of the present disclosure. Pull wires 606 may run along the length of elongate member 102, from its proximal end to its distal end, or the pull wires 606 may extend only along a distal portion of the elongate member 102. In one embodiment, pull wires 606 extend up to the proximal end of the sheath 602. In some instances, one or more of pull wires 606 may loop back on themselves to create yet another different profile. It should be understood that other expansion mechanisms, including springs, inflation balloon, etc., may also be employed. Further, a distal end portion of hood 600 may be reinforced with a ring to create a substantially smooth circular edge.

The distal portions of the wires in this embodiment are curved radially outwardly to create the outward urging force so that in the expanded state (FIG. 6C), when the expandable hood portion extends out of the distal end of the sheath 602, the expandable hood portion 604 spreads out to increase the working area of the hood 600. The entire lengths of the wires or the distal portions of pull wires 606 may be formed of shape memory materials such that in the normal state the distal portion of pull wires 606 curve outwardly from the central axis. When force is applied on the distal portions of pull wires 606, they may curve inward such that they are parallel to the central axis of the elongated member.

In operation, the expandable hood portion 604 remains within the sheath 602 when in the closed state. The sheath exerts a force on the wires maintaining them substantially straight within the sheath. An actuation mechanism, present at the proximal end of the elongate member 102, for instance as part of a handle, allows an operator to urge expandable hood portion 604 out of sheath 602 when the distal end 106 of the elongate member 102 is at the desired location within a patient's body. When expandable hood portion 604 extends beyond sheath 602, the sheath no longer exerts a force on the expandable hood portion, allowing the hood portion to curve outwardly.

In an alternate embodiment, the hood portions 604 may be self-expandable. The hood portion 604 may be disposed in a collapsed state within lumen defined by sheath 602. When appropriately positioned, sheath 602 may be pulled proximally allowing the hood 600 to extend distally from the sheath 602. As the hood 600 extends from the distal end of the sheath 604, the hood portions 604 expand into a preformed shape. In such embodiments, hood 600 may be formed of any suitable superelastic materials or shape memory material such as Nitinol.

Figure 7:
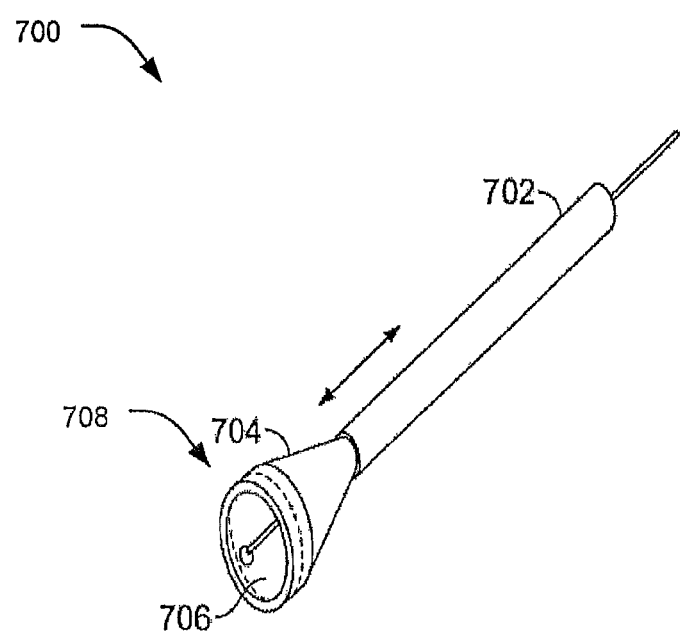
FIG. 7 is a perspective distal end view of yet another endoscopic hood, according to an embodiment of the present disclosure.
Figure 8:
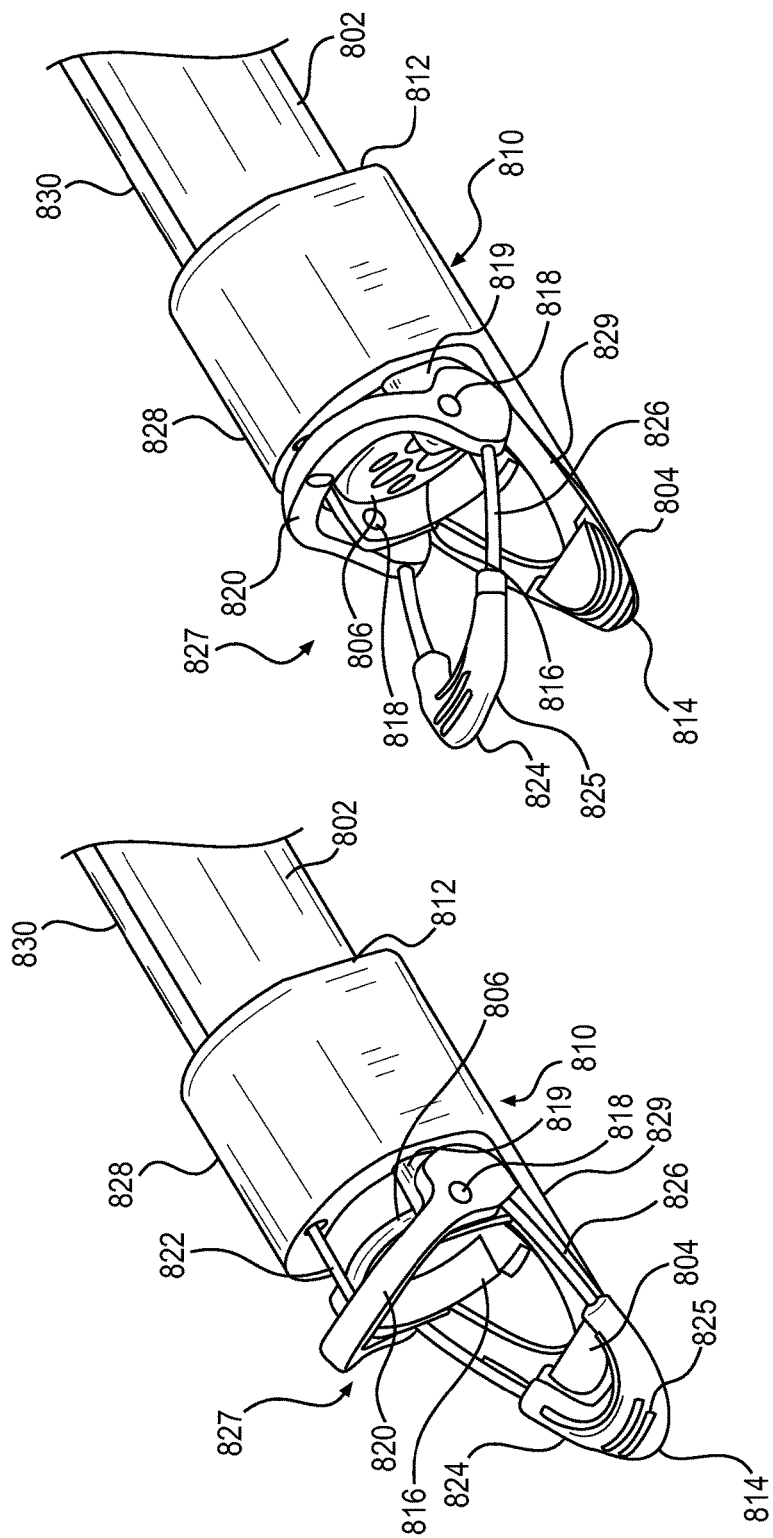
FIGS. 8A and 8B are perspective distal end views of an exemplary endoscopic cap in unactuated and actuated states, respectively, according to another embodiment of the present disclosure.

FIG. 7 is a perspective view of yet another embodiment of a hood. As noted above, any of the embodiments described herein may include one or more features of any of the other embodiments described herein. In this embodiment, hood 700 takes the form of a hollow cylinder, including an outer sheath 702 and an inner sheath 704. The inner sheath 704 is moveable between two positions—closed position (inside outer sheath 702), and expanded position (extending out of the distal end of outer sheath 702).

The inner sheath 704 may be formed of a self-expanding material, that when free of the force applied by outer sheath 702, expands into a distally flaring funnel. Any known self-expanding material may be utilized to form the inner sheath. For example, many flexible plastic materials having a memory will return to their natural relaxed state when constraining forces are removed. Thus, by forming such plastics material into a funnel shape, an inner expanding sheath can be provided that is constrained in its first position by the surrounding outer sheath 702 but will assume its funnel shape when extended from the outer sheath 702.

In another embodiment, inner sheath 704 may not be formed of a self-expanding member. In this case, the distal end 708 of inner sheath 704 may be selectively expanded by any suitable means. Suitable expansion mechanism may include, for example, springs, inflation balloon, etc. Alternatively, funnel may be removably coupled directly to the inner sheath 704. Funnel attachment means would be understood by a person of ordinary skill in the art.

One such means may be a cutting device, such as, e.g., a wire loop. In some embodiments, the cutting device may include cautery capabilities. Accordingly, the distal end of inner sheath 704 may include a circumferential channel 706, which may be connected to the elongate member's lumen through a small lumen (not shown) in the inner sheath 704. The cutting device may be inserted into channel 706 through the small lumen. By distally urging the cutting loop into circumferential channel 706, and by controlling the length of the cutting loop introduced into the channel 706, the distal diameter of inner sheath 704 may be varied. Thus, inner sheath 704 may be formed of a flexible member that is expandable when exposed to a force and contracts back to its original size once the expanding force is removed. In order to exert enough force to expand the inner sheath 704, the cutting loop should have certain rigidity. The required rigidity depends on the flexibility of inner sheath 704 and therefore, during manufacture, designers may consider the flexibility of inner sheath 704 and the rigidity of the cutting loop to design an effective expandable hood 700.

In the embodiments described with reference to FIGS. 2-7, any suitable material may be used to form the hood. For instance, rigid or semi-rigid materials such as metals (including shape-memory materials such as Nitinol), polymers, resins, super elastic materials, or plastics may be used. The hoods may also be optically transparent or translucent, allowing physicians to visualize the tissue being resected. Further, a biocompatible material that does not irritate the body lumens may be applied as a coating over the outer surfaces of the hoods.

Further, in all the embodiments described above, the hood is moveable between two states—closed and expanded. An actuation mechanism may be employed in all of the above embodiments to change the state of the hood. For example, the pull wires (in FIG. 6) may be coupled to an actuation mechanism on a handle. This mechanism may be a simple mechanical design such as a slider or a roller attached to the proximal ends of the pull wires. By moving the slider proximally or rotating the roller clockwise, the hood may be placed in the closed state, and by moving the slider distally or rotating the roller anti-clockwise, the hood may be placed in the expanded state. It will be understood that these mechanical mechanisms are merely illustrative and that other mechanical actuation mechanisms may instead be employed to actuate the hood.

In other embodiments, the actuation mechanism may be electronic or electromechanical, such as a digital touch pad, switch, or button. These and other actuation mechanisms are relatively well known in the art and will not be described any further in this disclosure. It will, however, be understood that any of these mechanisms may be employed to move the hood between its closed and its expanded state, without departing from the scope of the present disclosure.

By actuating the hood in its expanded state, encroaching tissue at the treatment site may be retracted providing more space for the operator to visualize and operate on the target tissue. Moreover, once the target tissue is dissected or resected, by placing the hood in its closed state, the dissected tissue may be captured in the hood and extracted with the endoscopic device when the device is retracted. By using the hood itself to behave as a grasper or a tissue capturing device, the need for a separate grasper or capturing tool may be eliminated. In such embodiments, the inner edges of the sections of the hood may include ridges, teeth, or other suitable geometric configurations to aid in tissue grasping and/or retraction. In minimally invasive and endoscopic procedures, where space is generally a constraint and time to exchange tools within the endoscope is a prime parameter in determining operating expense, utilizing the hood itself to grasp and retract tissue may be useful. In some embodiments, the dissected tissue may be extracted into the endoscopic device by suction mechanism.

The following section sets out an exemplary method for resecting lesions, polyps, or any other tissue from a patient's body. A typical location for a resection of this sort is the stomach, and that location will be discussed here. As will be understood by those in the art, other patient locations would be equally suitable. Either a percutaneous incision is made to access the gastrointestinal tract, or the resection device 100 may be inserted through a natural opening, such as the mouth.

Once inserted, the resection device 100 may be advanced to a location proximate the targeted tissue, e.g., a lesion located above the muscularis layer. During placement, a device with a hood embodiment disclosed herein, such as, e.g., hood 110, is maintained in the closed state such that it can pass through the small cavities within a patient's body without causing undue trauma. A steering mechanism may be incorporated in the resection device 100 (with controls in the handle) to guide and urge the device within a body cavity. A light source and a camera (not shown) may be inserted in the elongate member's lumen 108 to direct the device 100 within the stomach, and to identify target tissue, e.g., lesions. Various identification techniques may be employed. For example, a biomarker or dye may be applied around the gastrointestinal tract. Cancerous lesions, e.g., emit a different wavelength when light falls on them, allowing operators to easily detect them.

Once at the desired location, the hood 110 may be translated into its expanded state to push encroaching tissue away from the targeted tissue and increase the working volume of hood 110. The degree of expansion may be fixed, but in other cases, the degree of expansion may be configurable based on the size of the lesion. An actuation mechanism, present on the handle or a proximal portion of the elongate member, may be used to expand the hood and maintain it in the expanded state until the operation is complete or until such time as decided by the operator.

A grasper or suction may be provided through hood 110 to acquire the targeted tissue. Subsequently, the suction device may be powered off or removed, and a telescope or microscope (not shown) may be introduced into the elongated member 102, along with a light source (not shown), allowing a physician to closely examine the target tissue, and to determine whether the target tissue requires resection. Various other known techniques may be employed for this determination, without departing from the scope of the present disclosure.

Next, a resecting device, e.g., a cautery knife, snare loop, blade, ligating band or any other such tool, with or without energization, such as RF energy, may be introduced through hood 110 to sever the targeted tissue. Alternatively, the edges of the hood's distal opening may include resecting elements to cut tissue as the hood "closes" on the tissue.

Once the lesion is resected, device 100 may carry out any number of procedures to excise the resected matter. For example, resection device 100 may extract the lesion or morcellate it and then extract it. For extraction, hood 110 may simply be retracted to its closed state. While closing the hood 110 may grasp or capture the dissected tissue. Alternatively, a grasping or capturing device may be introduced into the hood 110 to extract the dissected tissue. In one embodiment, the lesion may be extracted with the help of suction force applied at proximal end 104 of resection device 100. In another embodiment, a basket, grasper, or pincers may be used.

FIGS. 8A-15C are distal end views of exemplary endoscopic distal portions, including caps in unactuated and actuated states for dissecting and/or resecting polyps, lesions, or other undesired tissue from the interior bodily walls of a patient. In these examples, the distal portions may include a moveable component (e.g., actuatable portion 827 of FIGS. 8A and 8B, bar 924 of FIGS. 9 and 10A-C, bar 1124 of FIG. 11, tissue lifter 1250 of FIGS. 12A-C, tissue lifter 1360 of FIGS. 13A-C, retractor arms 1470 of FIGS. 14A-C, and/or tissue retractor 1580 of FIGS. 15A-C) to lift tissue away from and/or out of the view of, the working area. This moveable component may be inserted between layers of tissue and used to expand the view of tissue hidden by other layers of the tissue. The moveable component may be actuated across a central longitudinal axis of the cap. Such as wide sweep across the distal face of the cap permits greater lifting/retraction of tissue. The moveable component may be actuated/rotated/etc. in the direction (up, down, left, right, etc. depending on the orientation of the distal portion and tissues) away from the tissue the user desires to view. In the examples shown in FIGS. 8A-15C, the moveable component may be inserted below tissue desired for retraction and above tissue desired to be viewed. The moveable component would then be actuated/rotated/moved in a direction away from the tissue desired to be viewed, lifting the tissue desired to be retracted.

The examples illustrated in FIGS. 8A through 15C may include an elongate member 802 having a proximal end (not shown), a distal end 806, and one or more lumens extending between the proximal end and distal end 806. The proximal end may be coupled to a handle (not shown), while distal end 806 may be permanently or removably coupled to a distal portion, including, but not limited to, any of the above described hoods, cap 810 of FIGS. 8A and 8B, cap 910 of FIGS. 9 and 10A-100, cap 1110 of FIG. 11, cap 1210 of FIGS. 12A-C, cap 1310 of FIGS. 13A-C, cap 1410 of FIGS. 14A-C, and/or cap 1510 of FIGS. 15A-C. In some examples, the disclosed distal portion, e.g., cap, may be made integrally with distal end 806 of elongate member 802. The distal portions may be temporarily or permanently attached to the elongate member's distal end 806. By configuring the caps to complementarily engage with the distal end of a conventional endoscope or catheter, the caps may be used with existing endoscopes and catheters. A permanently attached cap ensures that the cap does not inadvertently separate from the elongate member's distal end 806 during a procedure. On the other hand, however, a removably coupled cap may allow for utilizing caps of differing designs and/or sizes. Based on the desired application, caps may be manufactured either permanently attached to the distal end 806 of elongate member 802 or temporarily attach the cap to elongate member 802 having complementary attachment portions.

For temporary attachment, a proximal portion of the cap (e.g., attachment section 828 of cap 810) may include a substantially open attachment section, e.g., cylindrical, defining a recess for receiving a distal end 806 of elongate member 802. The recess may include threading, projections, grooves, or any other mechanism for temporarily attaching the desired cap to complementary structures on the elongate member. Thus, temporary attachments may, for instance, be defined by a screw-fit, Luer taper, snap-fit, or compression fit arrangement. In some examples, the attachment portion may be adjustable, allowing operators to connect elongate members of varying configurations or sizes to the cap. For instance, the attachment section may be formed of a flexible material, such as elastic or rubber, which may expand radially to allow the cap to fit over a range of elongate members with diameters greater than that of the cap's attachment section. It will be understood that the attachment section can be made from different materials and be configured differently to provide for adjustability without departing from the scope of the present disclosure. Furthermore, mechanisms for holding the attachment section to the endoscope may be used, including, e.g., hose clamps, crimp bands, wrapped filaments, clips, etc.

Permanent attachment may include welding, gluing, soldering, or other forms of attachment, or the desired cap may be integrally formed with elongate member 802. It will be appreciated that other forms of temporary or permanent attachment may be adopted without departing from the scope of the present disclosure. In some examples, the desired cap may be integral with a sheath which fits along a portion of the endoscope from the distal end and proximally. In further embodiments, this sheath may extend substantially the entire length of the endoscope.

Similar to elongate member 102, elongate member 802 may be any flexible or rigid member adapted to be inserted into a patient. Further, elongate member 802 may be flexible in certain portions and rigid in others. For example, the elongate member's distal end 806 may be flexible or steerable, allowing the member to traverse circuitous cavities or lumens, while the rest of member 802 may be rigid to allow the elongate member 802 to be inserted into a body cavity.

In the illustrated device, elongate member 802 has a generally circular cross-section, with one or more substantially circular hollow interior lumens, although not so limited in various embodiments. Indeed, elongate member 802 and/or any lumens within may have any suitable cross-sectional geometries, including, e.g., rectangular and/or ovular. Further, elongate member 802 may have a uniform diameter or may be tapered at the distal end 806 to facilitate insertion into a patient's body. Depending upon the particular implementation and intended use, the length and configuration of elongate member 802 may vary.

The elongate member 802 may be coated with lubricious materials and antibacterial agents to ease insertion into tight cavities and prevent infections, respectively. In addition, elongate member 802 may comprise lubricious materials or surface designs. Further, portions of the elongate member 802 may include radiopaque materials to visualize the position of elongate member 802 within a patient's body. Elongated member 802 described here may be any well-known endoscopic device used for colonoscopy, resectoscopy, cholangioscopy, mucosal resection, or other procedures, and thus, this device will not be discussed in detail in the remainder of the disclosure.

Elongate member 802 may include and/or connect to an auxiliary lumen 830. Auxiliary lumen 830 may be connected to elongate member 802 in any way, including, but not limited to, being integral with elongate member 802, attached at discrete locations along elongate member 802, or connected to elongate member 802 via a sleeve. Auxiliary lumen 830 may extend from the proximal end of elongate member 802 to the distal end 806 of elongate member 802 and/or a proximal end of a cap (e.g., proximal end 812 of cap 810 of FIGS. 8A and 8B). In some examples, auxiliary lumen 830 may not terminate at the distal end 806 of elongate member 802 and/or a proximal end of a cap, but instead extend distally of the proximal end of the cap and terminate proximal of the distal end of the cap (e.g., auxiliary lumen 1430 and 1431 of FIGS. 14A-C terminate distally of proximal end 1412 of cap 1410 and proximally of distal end 1414 of cap 1410). Auxiliary lumen 830 (and/or auxiliary lumens 1430 and 1431) may be a flexible tube, made from any suitable biocompatible material known to one of ordinary skill in the art and having sufficient flexibility to traverse tortuous anatomy in unison with elongate member 802. Such materials may include, but are not limited to, rubber, silicon, synthetic plastic, stainless steel, metal-polymer composites, and metal alloys of nickel, titanium, copper, cobalt, vanadium, chromium, and iron. In some examples, the material forming auxiliary lumen 830 may be a superelastic material such as Nitinol, which is a nickel-titanium alloy. In some embodiments, auxiliary lumen 830 may include layers of different materials and reinforcements. In some examples, elongate member 802 and auxiliary lumen 830 may be formed of the same material. In other examples, elongate member 802 and auxiliary lumen 830 may be formed of different materials. Auxiliary lumen 830 may have any cross-sectional shape and/or configuration and may be any desired dimension that can be received in a body cavity and/or connected to elongate member 802. In some embodiments, auxiliary lumen 830 may be made of, or coated with, a polymeric or lubricious material to enable auxiliary lumen 830 to pass through a body cavity with ease. The interior of auxiliary lumen 830 may have any suitable size, cross-sectional area, shape, and/or configuration to, for example, provide one or more actuation mechanism(s) 822 to distal end of auxiliary lumen 830. In some embodiments, the interior of auxiliary lumen 830 may be made of, or coated with, a polymeric or lubricious material to enable the actuation mechanism(s) 822 to slide through auxiliary lumen 830 with ease.

In some examples, the cap be coupled to include a mechanism 822 allowing a moveable component to transition between two states: a first state in which the moveable component (e.g., actuatable portion 827 of cap 810) is unactuated and/or in a position in which at least a portion of the moveable component can be inserted between layers of tissue, and a second state in which the moveable component is actuated and/or in a position in which at least a portion of moveable component lifts tissue away from adjacent tissue, away from the distal face of member 802, and/or so as to not obstruct the area in front of one or more lumens of elongate member 802 or tools within those lumens. The mechanism 822 may include pull wires, elongate tubes, springs, levers, hinges, pulleys, or other mechanisms for transitioning a moveable component of the cap from a first state to a second state. In one example, the transition from the first state to the second state is caused by actuation of an actuator at the proximal end that is connected to mechanism 822. Mechanism 822 may be one or more pull wires, and/or single or multiple rods. The wire(s) may be metallic, may be single stranded or multi-stranded. The rod(s) may be metallic, plastic, round, or square shape. Mechanism 822 may extend within auxiliary lumen 830 along the outside of elongate member 802 and may extend to a handle (not shown) for the user to manipulate. In some examples, the device may not include auxiliary lumen 830, and mechanism 822 may extend through a working channel of elongate member 802. Mechanism 822 (e.g., wire(s) and/or rod(s)) may be pushed/pulled to actuate an actuatable portion of a cap (e.g., cap 810 of FIGS. 8A and 8B, cap 910 of FIGS. 9 and 10A-10C, cap 1110 of FIG. 11, cap 1210 of FIGS. 12 A-C, cap 1310 of FIGS. 13A-C, cap 1410 of FIGS. 14A-C, and/or cap 1510 of FIGS. 15A-C).

FIGS. 8A-B illustrate elongate member 802 connected to cap 810. Cap 810 may be formed of any suitable biocompatible material, such as polyurethane, plastics, polymers, and metals including shape memory or superelastic materials, for instance Nitinol. Cap 810 may be coated with antibacterial and/or lubricious agents that prevent bacterial infections and/or allow cap 810 to easily pass through the lumens and cavities within a patient's body with minimal or no abrasion or bruising to surrounding tissue. Additionally or alternatively, cap 810 may comprise a lubricious material or surface, and/or surface designs that facilitate ease of insertion. The cap 810 has a proximal end 812 and a distal end 814. Cap 810 may include an attachment section 828, a base portion 829, and a moveable component, e.g., actuatable portion 827.

Attachment section 828 may be a generally tubular elongated member configured to be secured to the distal end 806 of elongate member 802. In the example depicted in FIGS. 8A and 8B, for example, attachment section 828 may be a proximal portion of cap 810 and may be configured to fit over distal end 806 of elongate member 802. Alternatively, attachment section 828 of cap 810 may be configured to fit into and extend from a lumen of elongated member 802. In some examples, the distal end 814 of attachment section 828 may be at the plane of the distal face of elongate member 802. In the example shown in FIGS. 8A and B, the distal end 814 of attachment section 828 may proximal and parallel to the distal face of elongate member 802. Attachment section 828 may include a lumen 816 extending from the cap's proximal end 812 to the proximal end of base portion 829. The longitudinal axis of lumen 816 may be parallel to and/or aligned with a longitudinal axis of elongate member 802. In some examples, attachment section 828 may include a second lumen. This second lumen may align with auxiliary lumen 830 and may be configured so that actuation mechanism 822 may extend to the distal end of attachment section 828. In some examples, attachment section 828 may utilize any of temporary or permanent attachment devices described above in order to attach attachment section 828 to elongate member 802.

Base portion 829 may be connected to a distal end of attachment section 828. Base portion 829 may be fixedly attached to or integrally formed with attachment section 828. Base portion 829 may have a uniform width or may be tapered from its proximal end to the distal end 814 to facilitate insertion between tissue layers. For example, a wall of base portion 829 (e.g., the bottom wall in FIGS. 8A and 8B) may extend from a wall of attachment section 828 (e.g., the bottom wall in FIGS. 8A and 8B). In some examples, the outer surface of the base portion wall may be congruent with the outer surface of the attachment section 828 and/or the outer surface of elongate member 802. In some examples, the outer surface of the base portion wall may be curved or may be substantially flat. A surface (e.g., an inwardly-facing upper surface) opposite the outer surface may extend at a downward angle away from the longitudinal axis of the attachment section toward the distal end 814. The angle may be between approximately 0 and 60 degrees. Base portion 829 may include a tissue gripping interface 804. Tissue gripping interface 804 may include multiple materials, micro-patterns, bumps, protrusions, a tacky surface, hooks, and/or materials of varying durometers.

Actuatable portion 827 (e.g., a moveable component) may pivotally connect to any portion of cap 810, including attachment section 828 and/or base portion 829. Alternatively, as shown in FIGS. 8A and 8B, actuatable portion 827 may be attached at pivot points 818 of tabs 819 by any rotatable fastener, including, for example, pins, screws, etc. Tabs 819 may, for example, extend distally of attachment section 828 and circumferentially from base portion 829. Actuatable portion 827 may include retracting arm 824 and actuating bar 820. Retracting arm 824 and actuating bar 820 may be fixed relative to each other. Retracting arm 824 may include a tissue gripping element 825, including multiple materials, micro-patterns, bumps, protrusions, a tacky surface, hooks, and/or materials of varying durometers. As shown in FIGS. 8A and 8B, retracting arm 824 may including a bar portion 826 on the proximal end and the tissue gripping element 825 on the distal end, e.g., covering portions of the bar portion 826.

In a first state, retracting arm 824 may contact the inwardly-facing upper surface of base portion 829 and may be configured to be inserted between a first layer and a second layer of tissue. Further, in the first state, retracting arm 824 may be parallel with and/or be flush against the upper surface of base portion 829. When transitioning from the first state to a second state, retracting arm 824 may cross the central longitudinal axis of cap 810. In a second state, retracting arm 824 may not contact the upper surface of the base portion 829, but instead be spaced apart from base portion 829. In the second state, retracting arm 824 may be in any position relative to the longitudinal axis of the attachment section 828, including but not limited to between below the longitudinal axis of the attachment section 828 or above the longitudinal axis of the attachment section 828. In the second state, actuating bar 820 may rotate toward the distal end of attachment section 828 and may eventually contact the distal end of attachment section 828 after sufficient proximal pulling by mechanism 822. In some examples, when fully rotated in the second state, actuating bar 820 may be contacting and/or be flush against the distal end of attachment section 828.

In one example, actuatable portion 827 may be moved/actuated from a first state, e.g., an unactuated state of FIG. 8A, to a second state, e.g., an actuated state of FIG. 8B, by a user pulling a proximal end of mechanism 822 (e.g., wire and/or rod) and thus pulling actuating bar 820 toward the distal end of attachment section 828. Moving from the first state to the second state may additionally or alternatively lift upper tissue layer(s) (e.g., layer(s) positioned radially inward of retracting arm 824) while keeping lower layer(s) (e.g., layer(s) positioned radially outward of base portion 829) stationary. Further, actuatable portion 827 may be moved/actuated/rotated from the second state, e.g., the actuated state of FIG. 8B, to a first state, e.g., the unactuated state of FIG. 8A, by a user pushing a proximal end of mechanism 822 (e.g., wire and/or rod) and thus pushing actuating bar 820 away from the distal end of attachment section 828.

FIG. 9 illustrates an alternative exemplary cap 910 with an attachment section 920, to attach cap 910 to elongate member 802, and a moveable component, e.g., bar 924 to manipulate tissue. Cap 910 may include any of the features of cap 810 described above. In addition, attachment section 920 may have any of the features of attachment section 820 of cap 810 and auxiliary lumen 930 may have any of the features of auxiliary lumen 830 of cap 810.

Similar to retracting arm 824 of FIGS. 8A and 8B, cap 910 includes a moveable component, bar 924. Bar 924 may be inserted between layers of tissue and, when actuated, lift tissue radially inward of bar 924, toward the longitudinal axis of attachment section 920 and/or elongate member 802. An actuation mechanism(s) (e.g., mechanism(s) 922) may be connected to bar 924, or may be an extensions of bar 924 and not separate components. In the example shown in FIG. 9, mechanism 922 may be two wires, each connected to one side of bar 924 on opposite sides of attachment section 920. The two wires 922 may extend through auxiliary lumen 930 independently. In other examples, the wires 922 may be secured to each other at or near the distal end of auxiliary lumen 930. Alternatively, the two wires 922 may connect to and terminate at a third wire or separate rod at or near the distal end of auxiliary lumen 930 and the third wire or separate rod may extend through auxiliary lumen 930 to the proximal/user-operated end. In one example, bar 924 may include a bend 925 between its proximal portion and distal portion. Mechanism 922 may connect at or near this bend 925. The bend 925 may be between approximately 120 degrees (as shown in FIG. 9) and approximately 60 degrees, or approximately 90 degree (as shown in FIGS. 10A-C). Bar 924 may pivotally connect to any portion of attachment section 920 of cap 910. As shown in FIGS. 9 and 10A-C, bar 924 may be attached at pivot points 918 by any rotatable fastener, including, for example, pins, screws, etc. Pivot points 918 may be approximately diametrically opposite (i.e. 180 degrees apart about the circumference of section 920) of located on an upper surface of attachment section 920 (i.e. less than 180 degrees apart).

FIGS. 10A-C illustrate bar 924 in an insertion state, partially actuated (e.g., actuated between an insertion state and a fully-actuated state), and the fully-actuated state, respectively. In FIG. 10A, bar 924 is in insertion state (e.g., for inserting into a patient's body or for inserting between layers of tissue) and the distal portion of bar 924 may be angled between approximately 40 and 80 degrees downward of the longitudinal axis of the attachment section 920, or approximately 60 degrees downward of the longitudinal axis of the attachment section 920. By pulling a proximal end of mechanism 922, a user may transition bar 924 from the angle of FIG. 10A to the angle of FIG. 10B. Bar 924 may be rotated to any angle between the insertion state angle and the fully-actuated state angle. FIG. 10C illustrates bar 924 in a fully-actuated state. In the fully-actuated state, the distal portion of bar 924 may be between approximately 40 and 120 degrees above the longitudinal axis of the attachment section 920, or approximately 80 degrees above the longitudinal axis of the attachment section 920. When transitioning from the insertion state to the fully-actuated state, bar 924 may cross the central longitudinal axis of cap 910. In one example, bar 924 may be rotated, by a user pulling a proximal end of mechanism 922 (e.g., wire and/or rod) and thus pulling bar 924 upward. Moving from the insertion state to the fully-actuated state may additionally or alternatively lift upper tissue layer(s) (e.g., layer(s) initially positioned radially inward of bar 924). Further, bar 924 may be moved/actuated/rotated from the fully-actuated state, e.g., FIG. 10C, to the insertion state, e.g., FIG. 10A, by a user pushing a proximal end of mechanism 922 (e.g., wire and/or rod) and thus pushing bar 924 in a downward direction.

Figure 11:
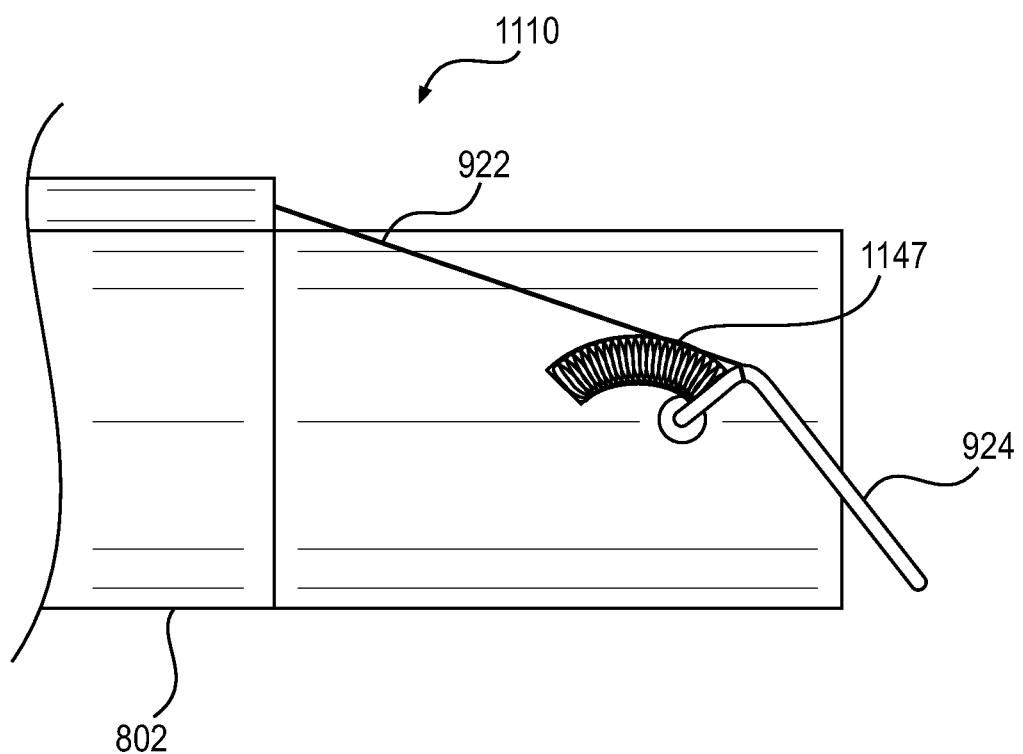
FIG. 11 is a side view of an alternative exemplary endoscopic cap including a moveable component biased in an unactuated state, according to another embodiment of the present disclosure.

In some examples, an element may be used in conjunction with any of the distal portions/caps described herein to bias the moveable component (e.g. bar 924) in a biased position. FIG. 11 illustrates an exemplary distal portion in which the moveable component is biased in the insertion state, e.g., the state of FIG. 10A. The biasing element may be placed distally within the patient on the cap, as shown in FIG. 11 or the biasing element may be external to the body of the patient at, for example, a user interface (not shown). As illustrated in FIG. 11, the biasing element may be a spring, e.g., spring 1147, on the distal portion (e.g. cap 1110) attached to or integral with elongate member 802. Additionally, a limiter (not shown) may be placed, such as in the handle or distally at the cap, to allow for the actuator, e.g. mechanism 922, to move the moveable component, e.g., bar 924, to specific positions. Spring 1147 is illustrated using an exemplary cap similar to cap 910, but any of the caps (e.g., cap 810, 1210, 1310, 1410 and/1510) may include a biasing element, including, but not limited to spring 1147.

FIGS. 12A-C illustrate an additional alternative exemplary distal portion, e.g., cap 1210 with an attachment section 1220 for attaching cap 1210, to elongate member 802, and a moveable component, e.g., tissue lifter 1250 to manipulate tissue. Cap 1210 may include any of the features of cap 810 described above. In addition, attachment section 1220 may have any of the features of attachment section 820 of cap 810.

Similar to retracting arm 824 of FIGS. 8A and 8B, tissue lifter 1250 may be inserted between layers of tissue and, when actuated, lift tissue layers that are above tissue lifter 1250. In some examples, tissue lifter 1250 may be a shield hinged to attachment section 1220. In one example, tissue lifter 1250 may include proximal portion 1252. Proximal portion 1252 may include a substantially flat top, as shown in FIGS. 12A-C or may have a shape substantially complementary to the exterior surface of attachment section 1220.

In an insertion state, tissue lifter 1250 may rest on top of attachment section 1220. The tissue lifter 1250 may include a distal portion 1251. Distal portion 1251 may extend at a downward angle from the remainder of tissue lifter 1250 (e.g., proximal portion 1252) toward the longitudinal axis of cap 1210. In the insertion state (e.g., as shown in FIGS. 12A-B), distal portion 1251 may extend at least partially over the distal face of lumen 1216. As shown in FIGS. 12A-C, distal portion 1251 may include a rounded or curved surface, but the shape of distal portion 1251 is not limited thereto.

An actuation mechanism (e.g., mechanism 1222) may be connected to tissue lifter 1250. Mechanism 1222 may connect at or near the proximal end of tissue lifter 1250. Tissue lifter 1250 may be pivotally connected to any portion of attachment section 1220 of cap 1210. As shown in FIGS. 12A-C, tissue lifter 1250 may be attached at pivot points 1218 by any rotatable fastener, including, for example, pins, screws, etc. Pivot points 1218 may be approximately diametrically opposite each other (i.e. 180 degrees apart about the circumference of section 1220) or located on an upper surface of attachment section 1220 (i.e. less than 180 degrees apart).

In the example shown in FIGS. 12A-C, mechanism 1222 may be two wires, each connected to one side of tissue lifter 1250 and above pivot points 1218. The two wires may include any of the features of wires 922 described above. FIGS. 12A-C illustrate tissue lifter 1250 in an insertion state (e.g., FIGS. 12A-B), and an actuated state (e.g., FIG. 12C). In FIGS. 12A and 12B, tissue lifter 1250 is in an insertion state, and the proximal portion 1252 of tissue lifter 1250 may contact and/or be flush against an outer surface of attachment section 1220. By pulling the proximal end of mechanism 1222, a user may transition tissue lifter 1250 from the position of FIGS. 12A and 12B to the actuated state of FIG. 12C. In the actuated state, proximal portion 1252 of tissue lifter 1250 may be spaced apart from the outer surface of attachment section 1220 and may be angled between approximately 10 degrees and approximately 40 degrees above the longitudinal axis of the attachment section 1220, or approximately 25 degrees above the longitudinal axis of the attachment section 1220. In one example, tissue lifter 1250 may be rotated by a user pulling a proximal end of mechanism 1222 (e.g., wire and/or rod) and thus pulling tissue lifter 1250 upward. When transitioning from the insertion state to the actuated state, tissue lifter 1250 may cross the central longitudinal axis of cap 1210. Moving from the insertion state to the actuated state may lift upper tissue layer(s). Further, tissue lifter 1250 may be moved/actuated/rotated from the actuated state, e.g., FIG. 12C, to insertion state, e.g., FIG. 12A, by a user pushing a proximal end of mechanism 1222 (e.g., wire and/or rod) and thus rotating tissue lifter 1250 in a downward direction, e.g., toward attachment section 1220.

FIGS. 13A-C illustrate an additional alternative exemplary distal portion, e.g., cap 1310. Cap 1310 may include an attachment section 1320 (for attaching cap 1310 to elongate member 802), and a moveable component e.g., tissue lifter 1360, to be inserted between tissue layers and/or manipulate these tissue layers. Cap 1310 may have any of the features of cap 810 described above. In addition, attachment section 1320 may have any of the features of attachment section 820 of cap 810.

Similar to retracting arm 824 of FIGS. 8A and 8B, tissue lifter 1360 may be inserted between layers of tissue and, when actuated, lift tissue layers that are above tissue lifter 1360. As shown in FIGS. 13A-C, tissue lifter 1360 may extend along the sides and in front of attachment section 1320 of cap 1310. In one example, tissue lifter 1360 may be approximately u-shaped crescent-shaped and include a gap 1361 between opposing sides of tissue lifter 1360 and proximal of the distal mid-portion of lifter 1360. Tissue lifter 1360 may be sized and shaped to allow the opposing sides of tissue lifter 1360 to be positioned radially outward of the walls of attachment section 1320 and the distal mid-portion to extend at least partially over the distal face of lumen 1316. As shown in FIGS. 13A-C, tissue lifter 1360 may have a tapered and/or curved distal end, but the shape of tissue lifter 1360 is not limited thereto. In some examples, lower edge 1362 of tissue lifter 1360 may be substantially straight along the side of lifter 1360 and, in an insertion state, lower edge 1362 may extend distally from pivot point 1318. An upper surface of tissue lifter 1360 is sloped downward (away from the actuation direction) from an inner curved edge to an outer curved edge.

Mechanism 1322 may connect at or near the proximal end of tissue lifter 1360. Mechanism 1322 may include any of the features of mechanism 822, mechanism 922, and/or mechanism 1222 described above. Tissue lifter 1360 may be pivotally connected to attachment section 1320 at, for example, pivot points 1318, and may be connected in any of the ways described above with respect to tissue lifter 1250 and cap 1210.

FIGS. 13A-C illustrate tissue lifter 1360 in an insertion state (e.g., FIGS. 13A-B), and an actuated state (e.g., FIG. 13C). In the insertion state, tissue lifter 1360 may extend distally of attachment section 1320 and/or may extend at least partially over the distal face of lumen 1316. Also, when in the insertion state, lower edges 1362 of tissue lifter 1360 may be angled downward of or be substantially parallel to the longitudinal axis of attachment section 1320. In the actuated state, tissue lifter 1360 may extend over less of the distal face of lumen 1316 than in the insertion state, or may not extend over any of the distal face of lumen 1316. Further, when in the actuated state, lower edges 1362 of tissue lifter 1360 may be between approximately 30 and 60 degrees above the longitudinal axis of the attachment section 1320, or approximately 45 degrees above the longitudinal axis of the attachment section 1320. When transitioning from the insertion state to the actuated state, tissue lifter 1360 may cross the central longitudinal axis of cap 1310.

FIGS. 14A-C illustrate an additional alternative exemplary distal portion, e.g., cap 1410. Cap 1410 may include attachment section 1420 for attaching cap 1410 to elongate member 802. Cap 1410 may include any of the features of cap 810 described above. In addition, attachment section 1420 may have any of the features of attachment section 820 of cap 810.

Cap 1410 may include at least one atraumatic tissue retracting arm, e.g., retracting arm(s) 1470, and/or a base portion 1428. As shown in FIGS. 14A-C, the interior of each of the distal ends of retracting arm(s) 1470 and base portion 1428 may include a pointed tip. The two pointed tips of retracting arms 1470 meet the two pointed tips of base portion 1428, when retracting arms 1470 are in an insertion state. The moveable component, e.g., retracting arm(s) 1470, may include, as shown in FIG. 14A, two separate arms. These arms 1470 may be spaced apart at their proximal ends at a distance greater than the diameter of attachment section 1420 so that the proximal ends of the arms 1470 can slide over an outer surface of attachment section 1420. As the arms 1470 extend distally, the arms 1470 may be angled toward each other and/or the longitudinal axis of attachment section 1420. The distal end 1415 of the arms 1470 may connect or may be connected by an addition segment 1472, as shown in FIG. 14A. The additional segment 1472 may be any shape, including, flat, curved, pointed, etc. In some examples, the space between arms 1470 may be filled, e.g., by additional material or arms 1470, instead of being distinct and separated with filled or unfilled space therebetween, may be a single monolithic piece without space therebetween. The material filling the space between arms 1470 may be flat or may be curved so that arms 1470 may slide over the outer surface of attachment section 1420.

Each arm of arms 1470 may be connected to an attachment arm 1474. The angle between each of retracting arms 1470 and its corresponding attachment arm 1474 may be between approximately 60 degrees and approximately 120 degrees, or approximately 90 degrees. Retracting arms 1470 may be attached to attachment arms 1474 in any way, including, but not limited to, fasteners, screws, nails, pins, welding, gluing, soldering, etc. In some examples, retracting arm(s) 1470 may be integral with attachment arms 1474. Attachments arms 1474 may be attached to the attachment section 1420 of cap 1410 at pivot points 1473. Pivot points 1473 may be at a first end of attachment arms 1474. Attachment arms 1474 may be attached at pivot points 1473 by any rotatable fastener, including, for example, pins, screws, etc. Pivot points 1418 may be approximately diametrically opposite each other (i.e. 180 degrees apart about the circumference of section 1420) or located on an upper surface of attachment section 1420 (i.e. less than 180 degrees apart).

Mechanism(s) 1422 may be connected to attachment arms 1474 at a second end, opposite the first end. Mechanism 1422 may include any of the features of mechanism 822, mechanism 922, and/or mechanism 1222 described above. Retracting arms 1470 may be actuated by mechanism 1422. In the example shown in FIGS. 14A-C, mechanism 1422 may be two wires, each connected to one side of the moveable component, e.g., one of retracting arms 1470 or one of attachment arms 1474. In some examples, the two wires 1422 may extend through a single auxiliary lumen, like in FIGS. 8A-13C. In other examples, the wires may each extend through a separate lumen, e.g., auxiliary lumens 1430 and 1431 of FIGS. 14A-C.

Retracting arms 1470 may be designed with mechanical advantage for lifting tissue. For example, a narrow distal end of the cap, e.g., distal end 1414 of cap 1410 may be inserted between layers of tissue. In an insertion state, e.g., FIGS. 14A and 14B, retracting arms 1470 may be angled in such a way that the endoscope, e.g., elongate member 802, may navigate smoothly through tissue. For example, the upper surface of retracting arms 1470 may be angled approximately 60 degrees to approximately 30 degrees relative the longitudinal axis of the attachment section 1420, or approximately 45 degrees relative to the longitudinal axis of the attachment section 1420. When transitioning from the insertion state to an actuated state, retracting arms 1470 may cross the central longitudinal axis of cap 1410. When actuated, retracting arms 1470 may lift tissue while a thin bottom piece of the cap, e.g., base portion 1428, may hold down tissue, causing the layers of tissue to be separated. Base portion 1428 may be continuous with attachment section 1420 or may be attached to attachment section 1420 in any way, including fasteners, screws, pins, welding, gluing, soldering, etc. At its proximal end, base portion 1428 attaches to a portion of the circumference of the distal end of attachment section 1420, from approximately 10 degrees to approximately 180 degrees of the circumference of the distal end of attachment section 1420, and in the example shown in FIG. 14A, approximately 60 degrees. Base 1428 may taper from its proximal end to its distal end, as shown in FIG. 14A. In some examples, the outer surface of base 1428 may be flat and/or may be substantially congruent with, and curved like, the outer surface of attachment section 1420. In some examples, cap 1410 may include a gap, e.g., gap 1490 between retracting arms 1470 and base 1428 to allow for tools to operate in the working area when retracting arms 1470 are unactuated, and continue to work in this space when retracting arms 1470 is actuated.

FIGS. 14A-C illustrate retracting arms 1470 in an insertion state (e.g., FIGS. 14A-B), and an actuated state (e.g., FIG. 14C). In FIGS. 14A and 14B, retracting arms 1470 are in an insertion state, and the distal end of retracting arms 1470 may contact the distal end of base portion 1428. By pulling the proximal end of mechanism(s) 1422, a user may rotate attachment arms 1474 and pull the second end of attachment arms 1474 proximally, thus transitioning retracting arms 1470 from the position of FIGS. 14A and 14B to the actuated state of FIG. 14C. In the actuated state, the attachment arms 1474 may be substantially perpendicular to the longitudinal axis of the attachment section 1420 and the retracting arms 1470 may be substantially parallel to the longitudinal axis of the attachment section 1420 or may be angled upward of the longitudinal axis of the attachment section 1420. In one example, attachment arms 1474 and thus retracting arms 1470 may be rotated by a user pulling a proximal end of mechanism(s) 1422 (e.g., wire and/or rod) and thus rotating retracting arms 1470 upward. Moving from the insertion state to the actuated state may lift upper tissue layer(s), e.g., any tissue the retracting arms 1470 were positioned under. Further, attachment arms 1474 and thus retracting arms 1470 may be moved/actuated/rotated from the actuated state, e.g., FIG. 14C, to insertion state, e.g., FIG. 14A, by a user pushing a proximal end of mechanism(s) 1422 (e.g., wires and/or rods) and thus rotating retracting arms 1470 in a downward direction, e.g., toward base portion 1428.

Figure 15A:
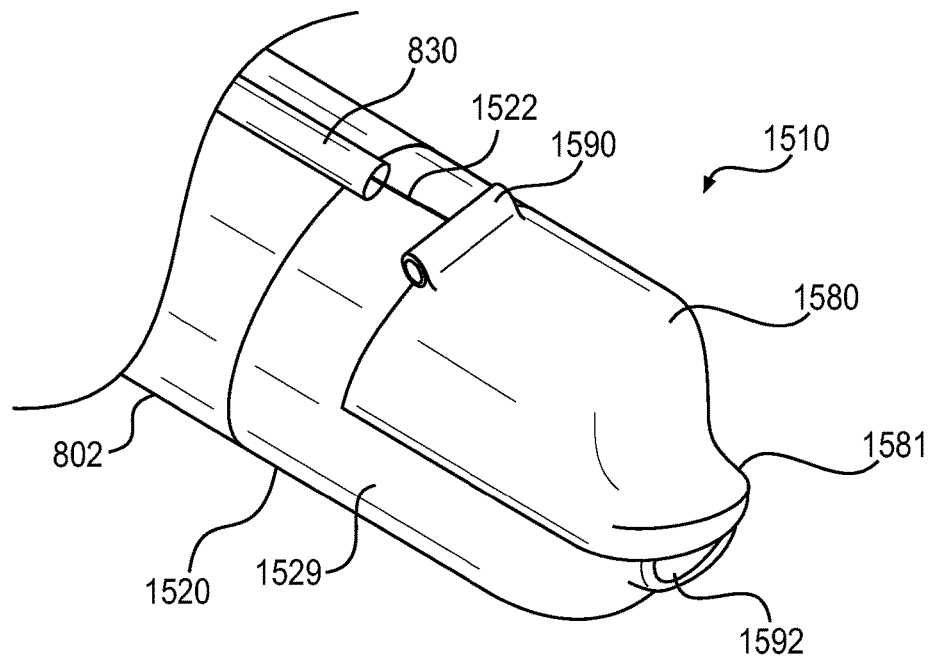
FIGS. 15A, 15B, and 15C are perspective and side views of an alternative exemplary endoscopic cap in unactuated and actuated states, according to another embodiment of the present disclosure.
Figure 15B:
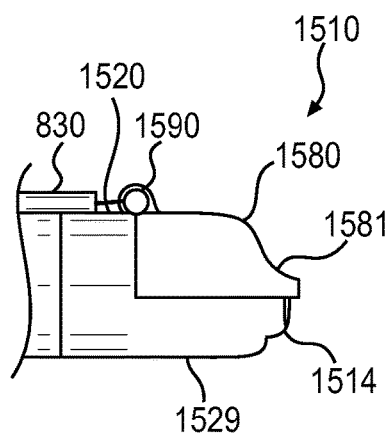
Figure 15C:
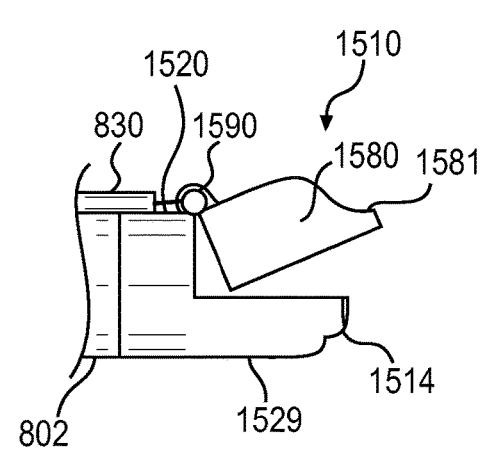

FIGS. 15A-C illustrate an additional alternative exemplary distal portion, e.g., cap 1510. Cap 1510 may include attachment section 1520 (for attaching cap 1510 to elongate member 802), a base portion 1529, and/or a moveable component, e.g., tissue retractor 1580. Cap 1510 may include any of the features of cap 810 described above.

Cap 1510 may include a moveable component, e.g., tissue retractor 1580. When unactuated, the narrow, distal end 1514 of cap 1510 and round edges of distal end 1514 may allow elongate member 802, e.g., an endoscope, to navigate smoothly through tissue and be inserted between layers of tissue. Tissue retractor 1580 may curve toward the longitudinal axis of attachment section 1520 at or near its distal end and may terminate in insertion portion 1581. Insertion portion 1581 may include a curved distal-facing end. When actuated, the moveable component, e.g., tissue retractor 1580 may retract tissue positioned above insertion portion 1581, expanding the view and increasing the size of the working area in front of member 802 and cap 1510. When transitioning from the insertion state to the actuated state, tissue retractor 1580 may cross the central longitudinal axis of cap 1510. Cap 1510 may include a gap, e.g., gap 1592, between the distal end of base portion 1529 and tissue retractor 1580. Gap 1592 may allow for tools to work in this space regardless of whether the moveable component, e.g., tissue retractor 1580, is unactuated or actuated.

Attachment section 1520 may have any of the features of attachment section 820 of cap 810. In addition, attachment section 1520 may be integral with base portion 1529. For example, a bottom half of attachment section 1520 may extend distally. A distal end of base portion 1529 may taper and/or curve inwardly toward the longitudinal axis. As shown in FIG. 15A, the distalmost end of base portion 1529 may include a cut-out, e.g., gap 1592. Gap 1592 may have any shape, including semicircular as shown in FIG. 15A.

At least a portion of tissue retractor 1580 (e.g., insertion portion 1581) may be inserted between layers of tissue and, when actuated, tissue retractor 1580 may lift tissue layers that are above tissue retractor 1580. The moveable component of cap 1510, e.g., tissue retractor 1580, may be actuated by mechanism 1522, e.g., wire(s), attached to a handle (not shown) at the user interface that runs through auxiliary lumen(s) 830. The moveable component, e.g., tissue retractor 1580 may be attached to other sections of cap 1510, e.g., attachment section 1520, by a hinge, e.g., hinge 1590. FIGS. 15A-C illustrate tissue retractor 1580 in an insertion state (e.g., FIGS. 15A-B), and an actuated state (e.g., FIG. 15C).

In FIGS. 15A and 15B, tissue retractor 1580 is in the insertion state and the bottom edge of tissue retractor 1580 may contact and/or be flush against an upper edge of base portion 1529, and/or a proximal edge of tissue retractor 1580 may contact and/or be flush against a distal edge of attachment section 1520. By pulling a proximal end of mechanism 1522, a user may transition the tissue retractor 1580 from the position of FIGS. 15A and 15B to the actuated state of FIG. 15C. In the actuated state, tissue retractor 1580 may be spaced apart from attachment section 1520 and/or base portion 1528 and may be angled between approximately 10 degrees and approximately 40 degrees above the longitudinal axis of the attachment section 1520, or approximately 25 degrees above the longitudinal axis of the attachment section 1520. In one example, tissue retractor 1580 may be rotated, by a user pulling a proximal end of mechanism 1522 (e.g., wire and/or rod) and thus pulling the tissue retractor 1580 upward. Moving from the insertion state to the actuated state may lift tissue layer(s) positioned above insertion portion 1581. Further, tissue retractor 1580 may be moved/actuated/rotated from the actuated state, e.g., FIG. 15C, to insertion state, e.g., FIG. 15A, by a user pushing a proximal end of mechanism 1522 (e.g., wire and/or rod) and thus rotating tissue retractor 1580 in a downward direction, e.g., toward attachment section 1520 and/or base portion 1529.

Embodiments of the present disclosure may be used in any medical or non-medical procedure, including any medical procedure where appropriate resection of an undesired body tissue is required. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with the true scope and spirit of the present disclosure being defined by the following claims.

What is claimed is:

1. A tissue retractor for attachment to a shaft of a medical device, the tissue retractor comprising:
    a cap having a central longitudinal axis, the cap comprising:
        an attachment section adapted to attach to a distal end of the shaft; and
        a moveable component pivotally attached to the attachment section at one or more pivot points; and
    an actuator connected to the moveable component to transition the moveable component from an insertion state to an actuated state by moving the moveable component first toward the central longitudinal axis in a first direction, and then away from the central longitudinal axis while still moving in the first direction.

2. The tissue retractor of claim 1, wherein the cap further includes a stationary portion contacting the moveable component at a distal end of the cap, the stationary portion configured to remain stationary relative to the attachment section when the moveable component transitions from the insertion state to the actuated state, wherein a first side of the stationary portion facing the central longitudinal axis slopes in a radially-outward direction from a proximal end of the stationary portion to a distal end of the stationary portion.

3. The tissue retractor of claim 2, wherein the moveable component includes a first portion and a second portion, and the first portion is approximately perpendicular to the second portion, is flush against the first side of the stationary portion in the insertion state, and is spaced apart from the first side of the stationary portion in the actuated state.

4. The tissue retractor of claim 3, wherein the moveable component is configured to move from the insertion state to the actuated state when a proximally-directed pulling force is applied to the actuator, and the moveable component is configured to move from the actuated state to the insertion state upon release of the proximally-directed pulling force or upon application of a distally-directed pushing force to the actuator.

5. The tissue retractor of claim 1, wherein the moveable component includes a gap for a tool to extend through and distally of the moveable component.

6. The tissue retractor of claim 1, wherein the cap is removably attached to the shaft.

7. The tissue retractor of claim 1, further comprising a biasing member configured to bias the moveable component in the insertion state.

8. A tissue retractor for attachment to a shaft of a medical device, the tissue retractor comprising:
    a cap having a central longitudinal axis, the cap including:
        an attachment section adapted to attach to a distal end of the shaft;
        a stationary component having a distal end that is fixed relative to the attachment section; and
        a moveable component pivotally attached to the attachment section at one or more pivot points; wherein:
            when in an insertion state, a distal end of the moveable component mates with the distal end of the stationary component,
            the moveable component includes a first portion and a second portion,
            the first portion is approximately perpendicular to the second portion, and
            when in the actuated state, the second portion contacts the attachment section;
        an actuator connected to the moveable component to pivot the moveable component away from the stationary component to transition the moveable component from the insertion state to an actuated state.

9. The tissue retractor of claim 8, wherein the moveable component includes a gap for a tool to extend through and distally of the moveable component.

10. The tissue retractor of claim 8, wherein the stationary component tapers from a proximal end of the stationary component to a distal end of the stationary component.

11. The tissue retractor of claim 8, wherein the cap is removably attached to the shaft.

12. The tissue retractor of claim 8, wherein at least a portion of the moveable component is a bar, and the bar pivots across the central longitudinal axis.

13. The tissue retractor of claim 8, wherein, when in the insertion state, the moveable component contacts the stationary component.

14. The tissue retractor of claim 8, wherein, when transitioning from the insertion state to the actuated state, the movable component moves first toward the central longitudinal axis in a first direction, and then away from the central longitudinal axis in the first direction.

15. A method of retracting tissue, comprising:
   inserting a cap into a body, wherein the cap has a central longitudinal axis and includes a moveable component and an attachment section;
   placing the moveable component between a first layer of tissue and a second layer of tissue; and
   actuating an actuation mechanism proximally to rotate the moveable component first toward, and then away from, the central longitudinal axis in a same direction to lift the first layer of tissue away from the second layer.

16. The method of claim 15, wherein the cap includes a stationary portion, and, during the step of actuating the actuation mechanism, the moveable component rotates away from the stationary portion.

17. The method of claim 16, wherein, prior to the step of actuating the actuation mechanism, the moveable component contacts the stationary portion.

18. The method of claim 16, further comprising:
   inserting the stationary portion between the first layer of tissue and the second layer of tissue.

* * * * *